United States Patent
Lee et al.

(10) Patent No.: US 11,833,504 B2
(45) Date of Patent: Dec. 5, 2023

(54) MICROFLUIDIC LABEL-FREE ISOLATION AND IDENTIFICATION OF CELLS USING FLUORESCENCE LIFETIME IMAGING (FLIM)

(71) Applicants: THE REGENTS OF THE UNIVERSITY OF CALIFORNIA, Oakland, CA (US); PIONEER HI-BRED INTERNATIONAL, INC., Johnston, IA (US)

(72) Inventors: Abraham P. Lee, Irvine, CA (US); Michelle A. Digman, Irvine, CA (US); Dohyun Lee, Irvine, CA (US); Xuan Li, Irvine, CA (US); Ning Ma, Irvine, CA (US); Yue Yun, Johnston, IA (US)

(73) Assignees: THE REGENTS OF THE UNIVERSITY OF CALIFORNIA, Oakland, CA (US); PIONEER HI-BRED INTERNATIONAL, INC., Johnston, IA (US)

( * ) Notice: Subject to any disclaimer, the term of this patent is extended or adjusted under 35 U.S.C. 154(b) by 678 days.

(21) Appl. No.: 16/847,305

(22) Filed: Apr. 13, 2020

(65) Prior Publication Data
US 2020/0238288 A1 Jul. 30, 2020

Related U.S. Application Data

(63) Continuation-in-part of application No. PCT/US2018/055722, filed on Oct. 12, 2018.
(Continued)

(51) Int. Cl.
*B01L 3/00* (2006.01)
*C12N 15/10* (2006.01)
*C12Q 1/02* (2006.01)

(52) U.S. Cl.
CPC ... *B01L 3/502761* (2013.01); *B01L 3/502715* (2013.01); *C12N 15/1003* (2013.01);
(Continued)

(58) Field of Classification Search
CPC ......... B01L 3/502761; B01L 3/502715; B01L 2200/0647; B01L 2300/0627;
(Continued)

(56) References Cited

U.S. PATENT DOCUMENTS 2,656,508 A 10/1953 Coulter
3,380,584 A 4/1968 Fulwyler
(Continued)

FOREIGN PATENT DOCUMENTS

GB 2395196 5/2004
WO WO2007120240 A2 10/2007
(Continued)

OTHER PUBLICATIONS

Winiarczyk et al., Comparative studies of live tapetum cells in sterile garlic (*Allium sativum*) and fertile leek (*Allium ampeloprasum*) using the fluorescence lifetime imaging analytical method, Jun. 6, 2018, Elsevier, South African Journal of Botany, 117, 222-231. (Year: 2018).*
(Continued)

*Primary Examiner* — Jennifer Wecker
*Assistant Examiner* — Kathryn Elizabeth Limbaugh
(74) *Attorney, Agent, or Firm* — NGUYEN TARBET LLC

(57) ABSTRACT

Methods and devices for single cell analysis using fluorescence lifetime imaging microscopy (FLIM) are disclosed. The methods utilize microfluidic devices which use traps to immobilize cells for FLIM analysis. The analysed cells may be sorted before or after imaging and may be plant, animal, or bacterial cells. Analysis of the FLIM data may use a
(Continued)

phasor plot and may be used to identify a metabolic pattern of the single cells.

15 Claims, 21 Drawing Sheets
(18 of 21 Drawing Sheet(s) Filed in Color)

Related U.S. Application Data

(60) Provisional application No. 62/571,746, filed on Oct. 12, 2017.

(52) U.S. Cl.
CPC ........ *C12Q 1/02* (2013.01); *B01L 2200/0647* (2013.01); *B01L 2300/0627* (2013.01); *B01L 2300/0816* (2013.01); *B01L 2300/0854* (2013.01); *B01L 2300/0858* (2013.01); *B01L 2300/0864* (2013.01)

(58) Field of Classification Search
CPC ..... B01L 2300/0816; B01L 2300/0854; B01L 2300/0858; B01L 2300/0864; C12N 15/1003; C12Q 1/02
See application file for complete search history.

(56) References Cited

U.S. PATENT DOCUMENTS

| | | | |
|---|---|---|---|
| 4,009,435 | A | 2/1977 | Hogg |
| 5,465,582 | A | 11/1995 | Bliss et al. |
| 8,263,023 | B2 | 9/2012 | Le Vot et al. |
| 8,365,311 | B2 | 1/2013 | Nawarathna |
| 8,927,040 | B2 | 1/2015 | Brand et al. |
| 9,176,504 | B2 | 11/2015 | Chiou et al. |
| 2002/0182654 | A1 | 12/2002 | Jing et al. |
| 2004/0234588 | A1 | 11/2004 | Lu et al. |
| 2005/0015001 | A1 | 1/2005 | Lec et al. |
| 2005/0106064 | A1 | 5/2005 | Laurell et al. |
| 2005/0272039 | A1 | 12/2005 | Yasuda |
| 2005/0272096 | A1 | 12/2005 | Clague et al. |
| 2006/0051329 | A1 | 3/2006 | Lee et al. |
| 2006/0177815 | A1 | 8/2006 | Soh et al. |
| 2007/0264320 | A1 | 11/2007 | Lee et al. |
| 2008/0038807 | A1 | 2/2008 | Pommersheim |
| 2008/0241875 | A1 | 10/2008 | Hwang et al. |
| 2009/0042310 | A1 | 2/2009 | Ward et al. |
| 2009/0068170 | A1 | 3/2009 | Weitz et al. |
| 2009/0075390 | A1 | 3/2009 | Linder et al. |
| 2009/0144860 | A1* | 6/2009 | Beeckman ......... C12N 15/8267 536/23.6 |
| 2009/0286300 | A1 | 11/2009 | Le Vot et al. |
| 2009/0298191 | A1 | 12/2009 | Whitesides et al. |
| 2011/0014606 | A1* | 1/2011 | Steinmetzer ......... B01J 19/0046 435/287.2 |
| 2011/0059556 | A1 | 3/2011 | Strey et al. |
| 2011/0086352 | A1 | 4/2011 | Bashir et al. |
| 2011/0285042 | A1 | 11/2011 | Viovy et al. |
| 2012/0034155 | A1 | 2/2012 | Hyde et al. |
| 2012/0107912 | A1 | 5/2012 | Hwang et al. |
| 2012/0196288 | A1 | 8/2012 | Beer |
| 2013/0078163 | A1 | 3/2013 | Chung et al. |
| 2013/0154671 | A1 | 6/2013 | Lee et al. |
| 2013/0171628 | A1 | 7/2013 | Di Carlo et al. |
| 2013/0210649 | A1 | 8/2013 | McKnight et al. |
| 2014/0011291 | A1 | 1/2014 | Patel et al. |
| 2014/0068797 | A1 | 3/2014 | Doudna et al. |
| 2014/0076430 | A1 | 3/2014 | Miller et al. |
| 2015/0018226 | A1 | 1/2015 | Hansen et al. |
| 2016/0033378 | A1 | 2/2016 | Husain et al. |
| 2016/0123858 | A1 | 5/2016 | Kapur et al. |
| 2016/0202153 | A1 | 7/2016 | Gadini et al. |
| 2017/0014449 | A1 | 1/2017 | Bangera et al. |
| 2017/0128940 | A1 | 5/2017 | Amini et al. |
| 2017/0128941 | A1* | 5/2017 | Sadri ................ B01L 3/502776 |
| 2017/0145169 | A1 | 5/2017 | Oakey et al. |
| 2017/0183722 | A1 | 6/2017 | Link |
| 2018/0030515 | A1 | 2/2018 | Regev et al. |
| 2018/0078940 | A1 | 3/2018 | Lee et al. |
| 2020/0156071 | A1* | 5/2020 | Hansen ............ G01N 33/54366 |

FOREIGN PATENT DOCUMENTS

| | | |
|---|---|---|
| WO | WO2015157567 A1 | 10/2015 |
| WO | WO2016040476 A1 | 3/2016 |
| WO | WO2016126871 A2 | 8/2016 |
| WO | WO2017070169 A1 | 4/2017 |

OTHER PUBLICATIONS

International Search Report for PCT Application No. PCT/US18/56852 dated Jan. 11, 2019.

Lin, R., et al. "High efficiency cell encapsulation utilizing novel on-demand droplet generation scheme and impedance-based detection." 14th international conference on miniaturized systems for chemistry and life sciences, ed. H. Andersson-Svahn, S. Verpoorte, J. Emineus, N. Pam me. 2010.

J. Kim, M. Chung, S. Kim, D. H. Jo, J. H. Kim, and N. L. Jeon, "Engineering of a Biomimetic Pericyte-Covered 3D Microvascular Network," Plos One, vol. 10, p. e0133880, 2015.

X. Wang, D. T. T. Phan, A. Sobrino, S. C. George, C. C. W. Hughes, and A. P. Lee, "Engineering anastomosis between living capillary networks and endothelial cell-lined microfluidic channels," Lab on a Chip, vol. 16, pp. 282-290, 2016.

Mazutis, L. et al., Lab on a Chip, vol. 9, pp. 2665-2672 (2009).

Simon, M.G. et al., Label-Free Detection of DNA Amplification in Dropletsusing Electrical Impedance, 15th International Conference on Miniaturized Systems for Chemistry and Life Sciences 2011 (MicroTAS 2011), pp. 1683-1685 (Year: 2011).

Marsh et al. Room temperature ionic liquids and their mixtures—a review. Fluid Phase Equilibria 219 (2004) 93-98.

Oh, Woon Su, "Synthesis and applications of imidazolium-based ionic liquids and their polymer derivatives" (2012). Doctoral Dissertations. 1958. http://scholarsmine.mst.edu/doctoral_dissertations/1958.

Baret et al., "Fluorescence-activated droplet sorting (FADS): efficient microfluidic cell sorting based on enzymatic activity," Lab Chip. Jul. 7, 2009; 9(13):1850-8. doi: 10.1039/b902504a. Epub Apr. 23, 2009.

Macosko et al., "Highly Parallel Genome-wide Expression Profiling of Individual Cells Using Nanoliter, Droplets," Cell, vol. 161, No. 5, pp. 1202-1214, May 2015.

International Search Report for PCT Application No. PCT/2018/36962 dated Aug. 30, 2018.

International Search Report for PCT Application No. PCT/2018/36952 dated Sep. 18, 2018.

Kamalakshakurup et al. High-efficiency single cell encapsulation and size selective capture of cells in picoliter droplets based on hydrodynamic micro-vortices. Lab Chip, 2017, 17, 4324-4333.

Brouzes, Eric, et al. "Droplet microfluidic technology for single-cell high-throughput screening." Proceedings of the National Academy of Sciences106.34 (2009): 14195-14200.

S. I. Rubinow and J. B. Keller, "The transverse force on a spinning sphere moving in a viscous fluid," J. Fluid Mech., vol. 11, No. 03, p. 447, Nov. 1961.

Murata et al., Electrochemical single-cell gene-expression assay combining dielectrophoretic manipulation with secreted alkaline phosphatase reporter system, 2009, Biosensors and Bioelectronics, 25, 913-919.

Stinson et al., Genes Expressed in the Male Gametophyte of Flowering Plants and Their Isolation, 1987, Plant Physiol., 83, 442-447.

International Search Report for PCT Application No. PCT/US2016/056683 dated Dec. 27, 2016.

International Search Report for PCT Application No. PCT/2018/55722 dated Feb. 6, 2019.

(56) References Cited

OTHER PUBLICATIONS

International Search Report for PCT Application No. PCT/2017/55984 dated Dec. 14, 2017.
Doria, Arlene et al., "Rapid blood plasma separation with air-liquid cavity acoustic transducers", 15th International conference on miniaturized systems for chemistry and life sciences, Oct. 2-6, 2011, pp. 1882-1884.
Lee, Abraham P. et al., "Microfluidic air-liquid cavity acoustic transducers for on-chip integration of sample preparation and sample detection", Journal of laboratory automation, Dec. 2010, vol. 15, No. 6, pp. 449-454.
International Search Report Issued for PCT Application No. PCT/US2013/042735 dated Sep. 13, 2013.
Kobel et al. Optimization of microfluidic single cell trapping for long-term on-chip culture, Lab Chip, Jan. 13, 2010, 10, 857-863.

* cited by examiner

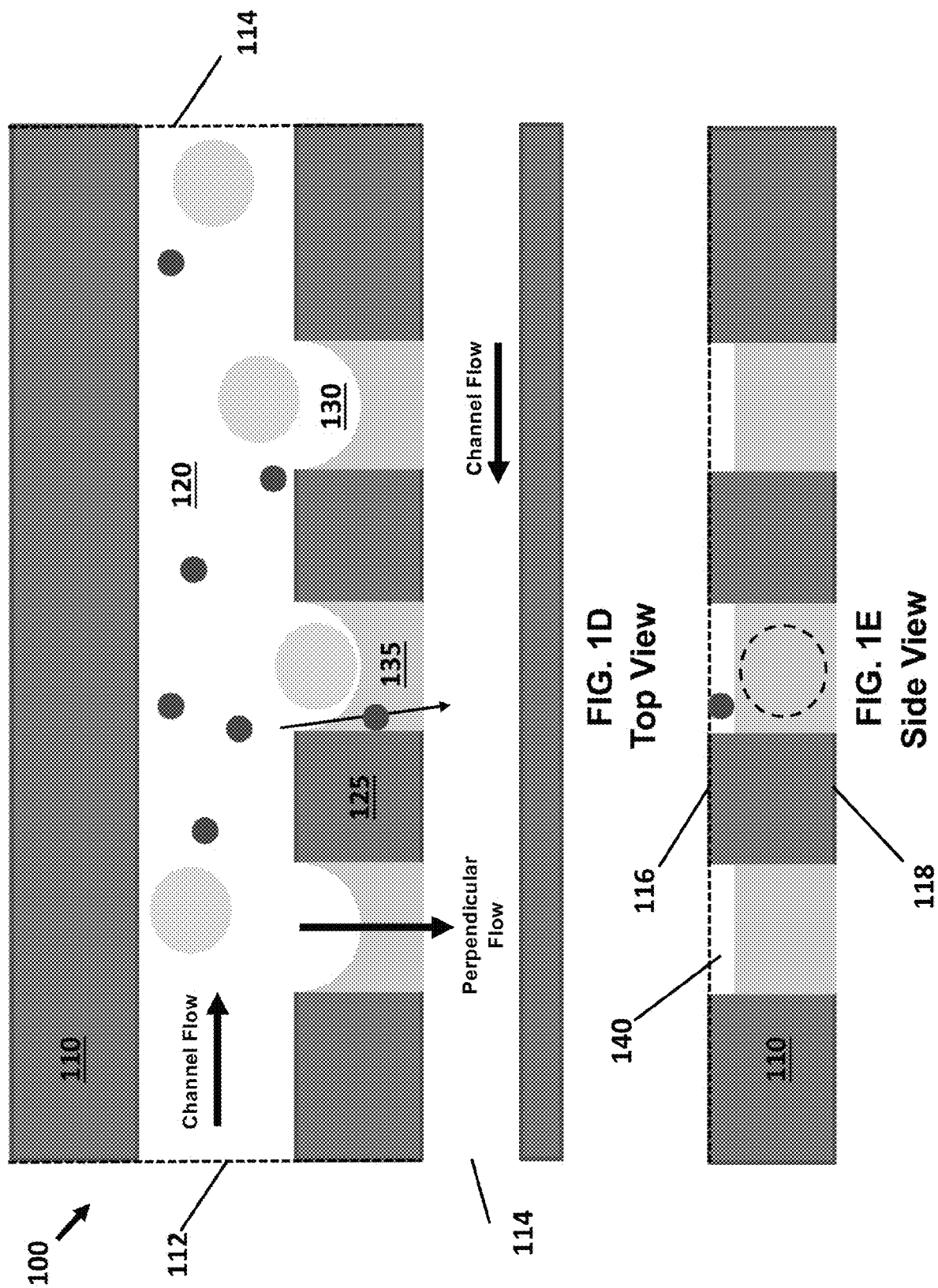

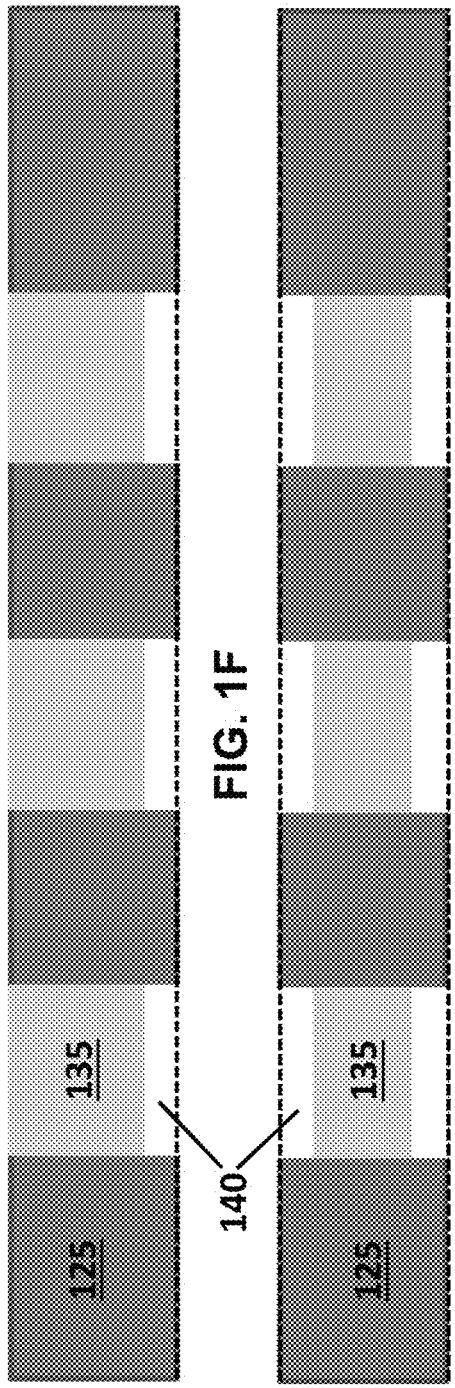
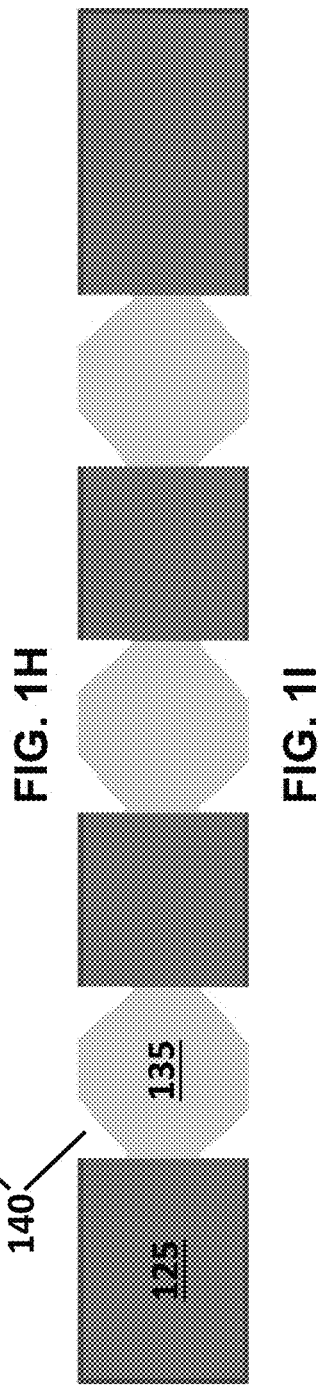
FIG. 1F    FIG. 1G    FIG. 1H    FIG. 1I

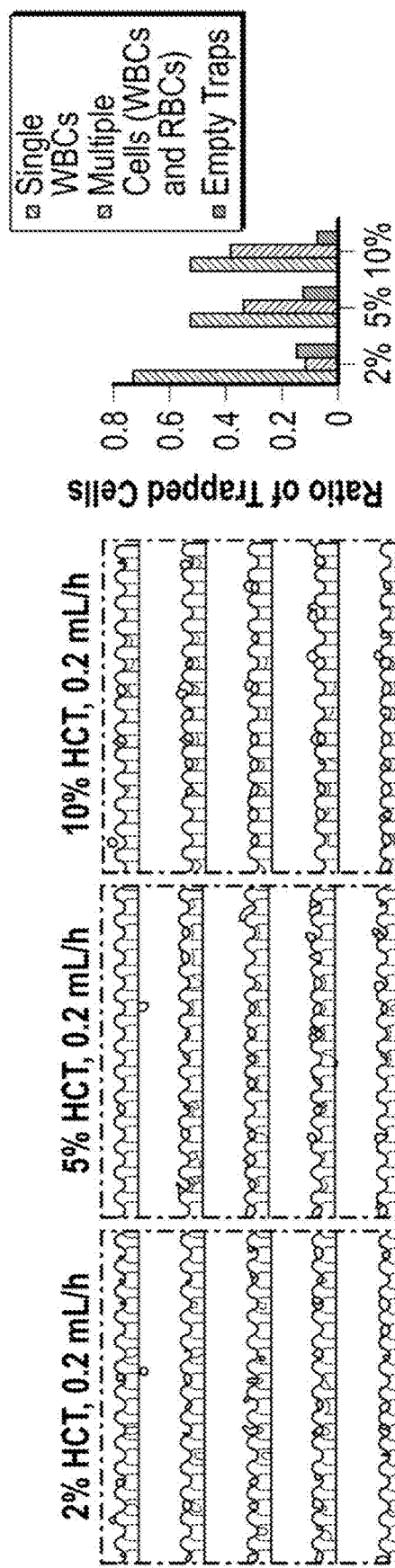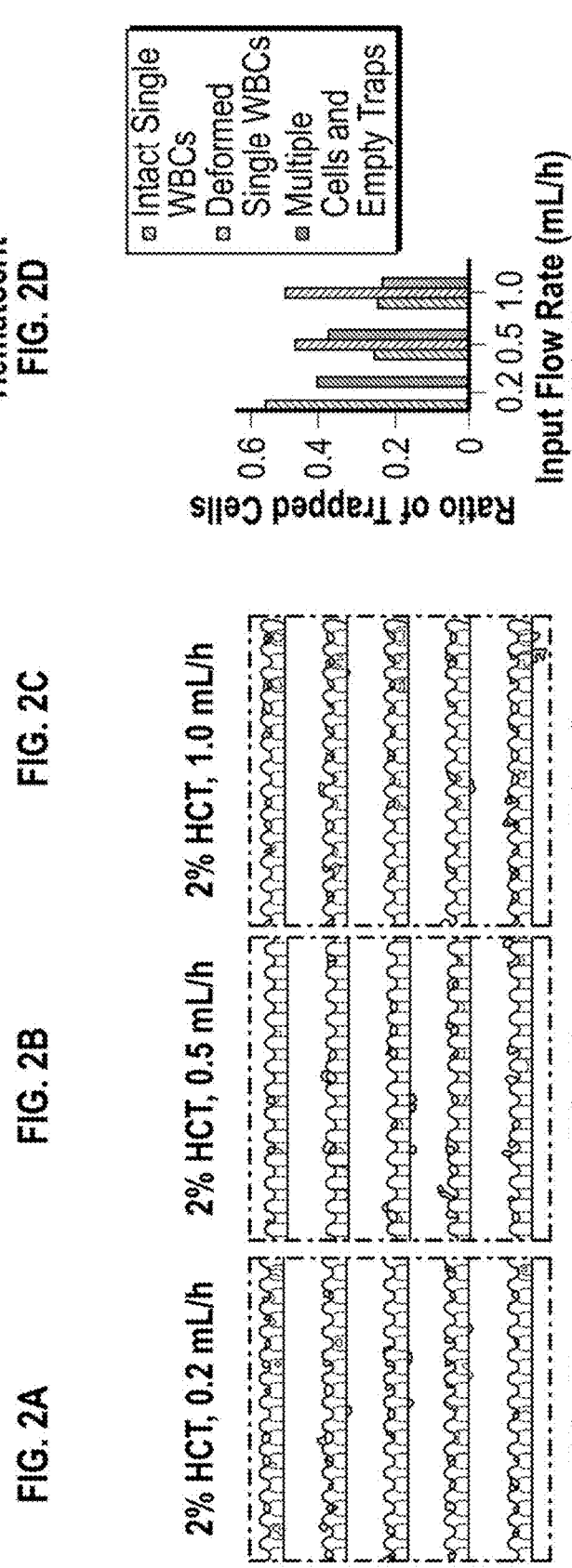

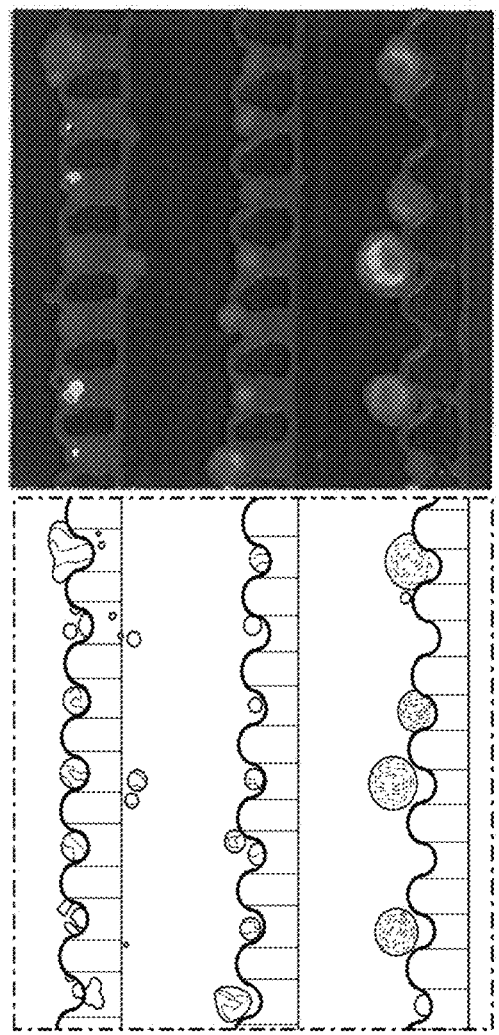
FIG. 4A
FIG. 4B
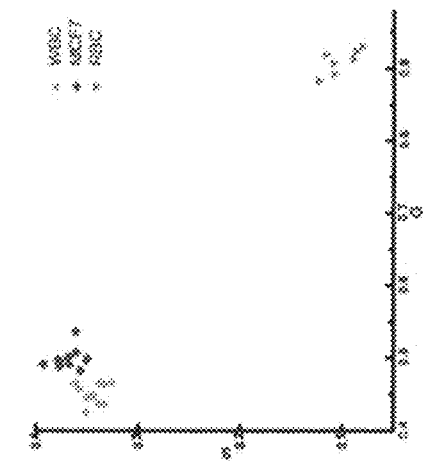
FIG. 4E
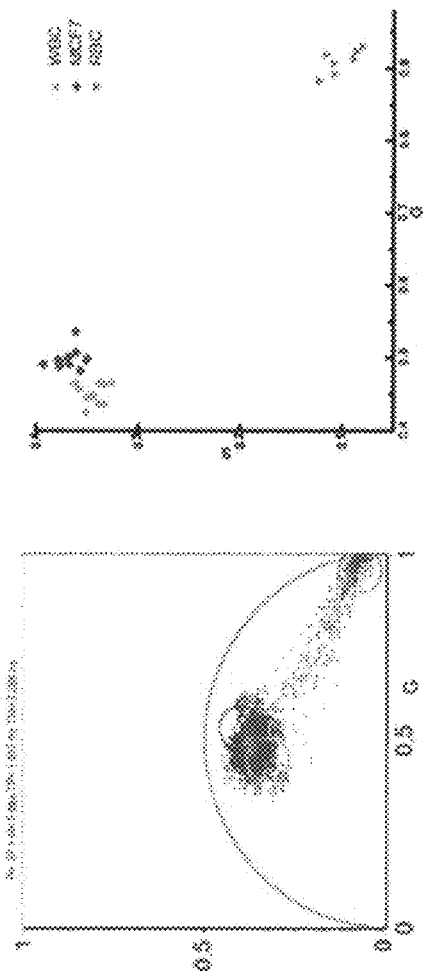
FIG. 4D
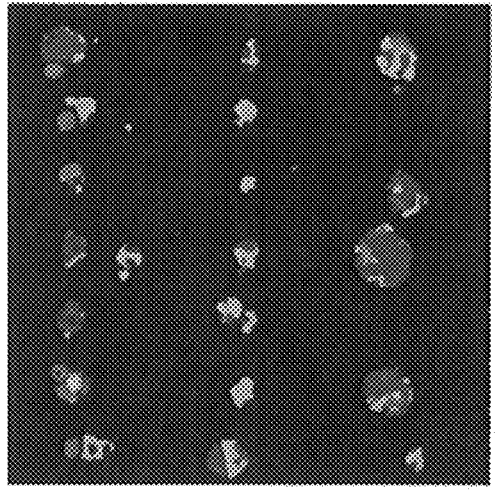
FIG. 4C

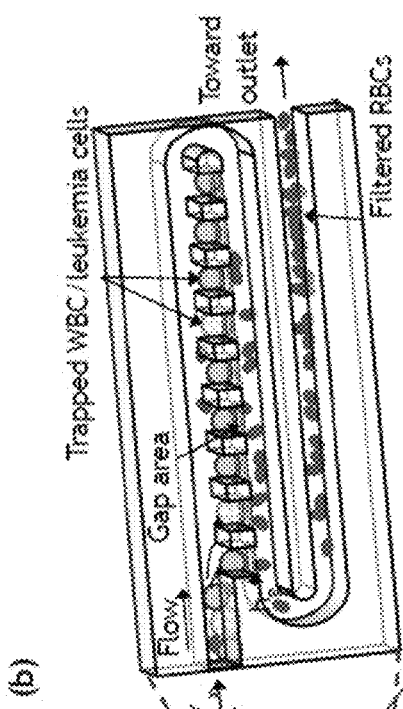
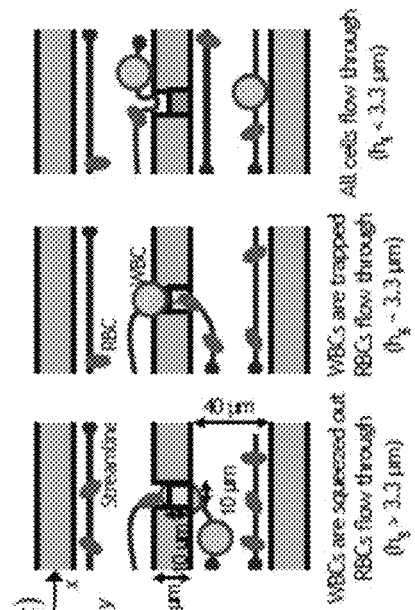
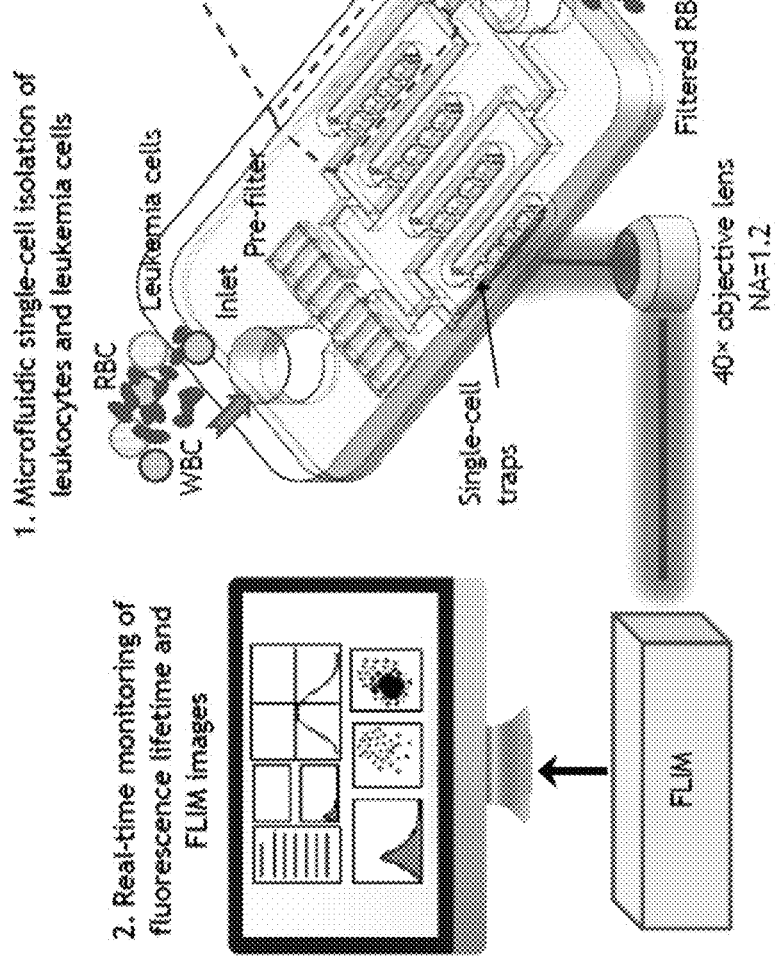
FIG. 5A
FIG. 5B
FIG. 5C

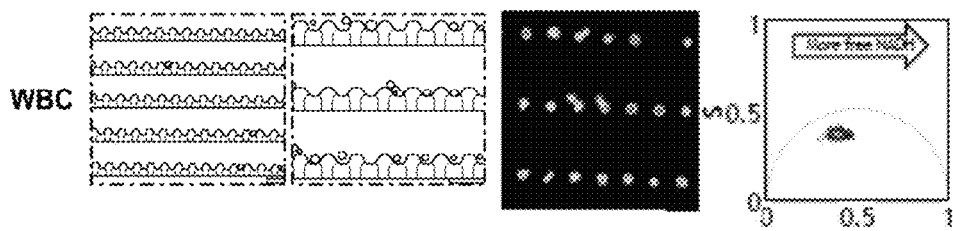
FIG. 7A WBC
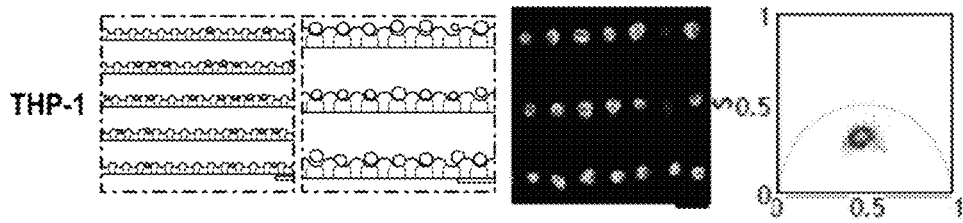
FIG. 7B THP-1
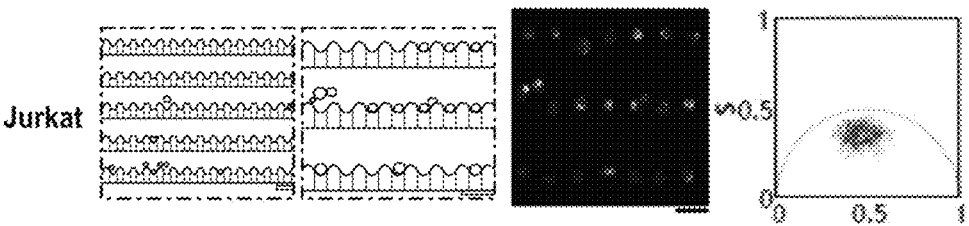
FIG. 7C Jurkat
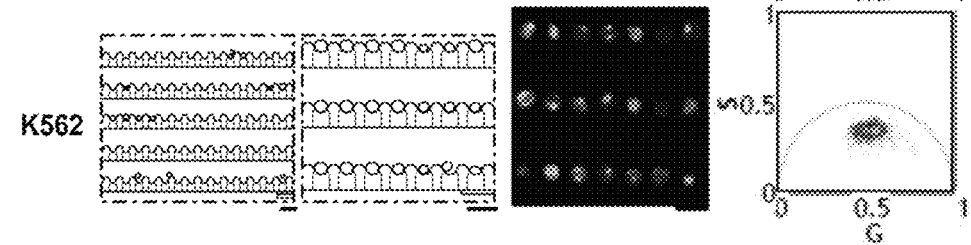
FIG. 7D K562
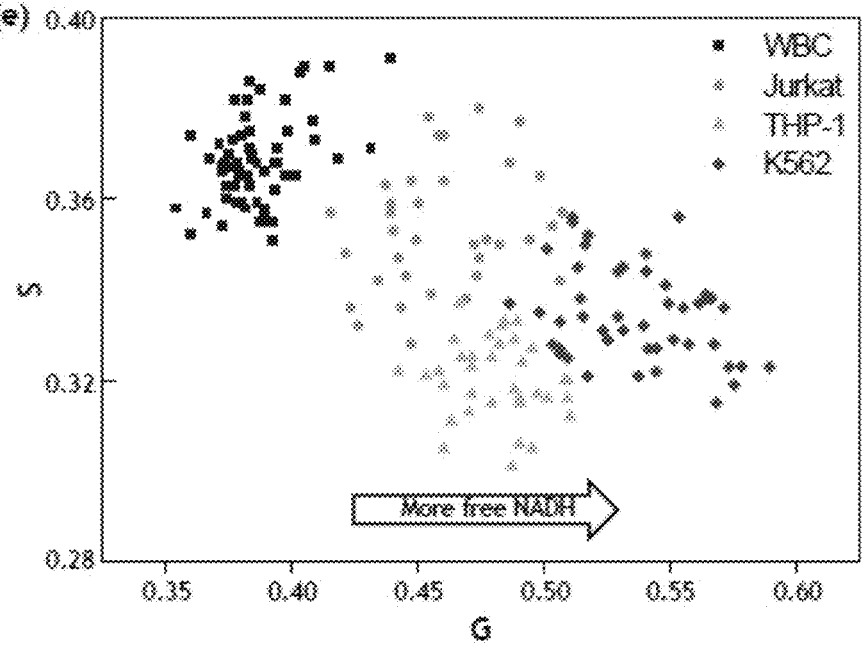
FIG. 7E
Scale bar: 50 um

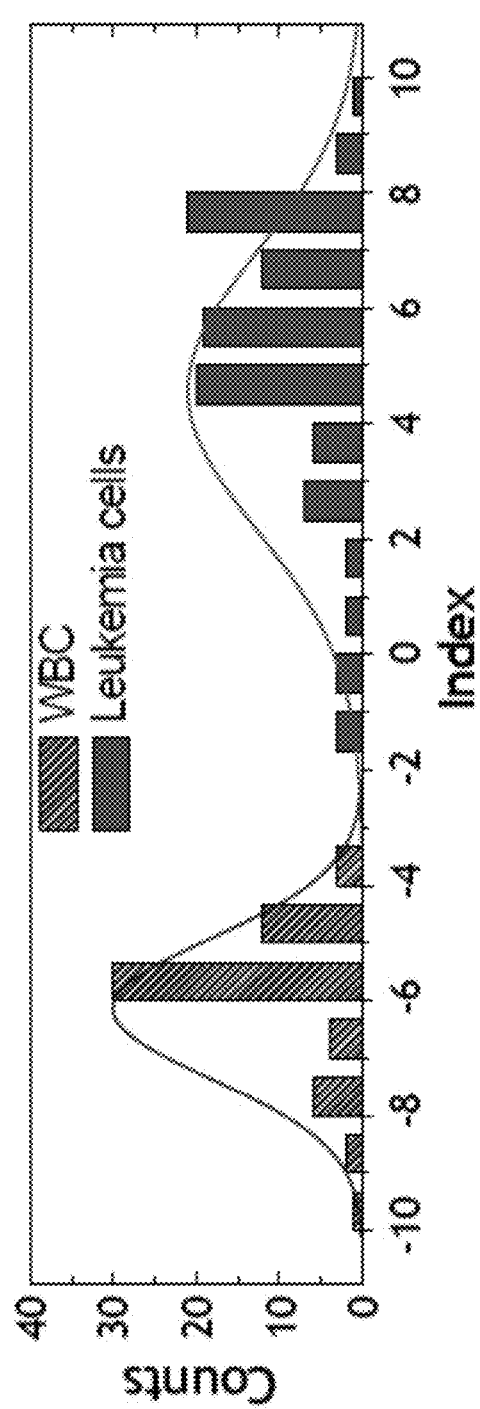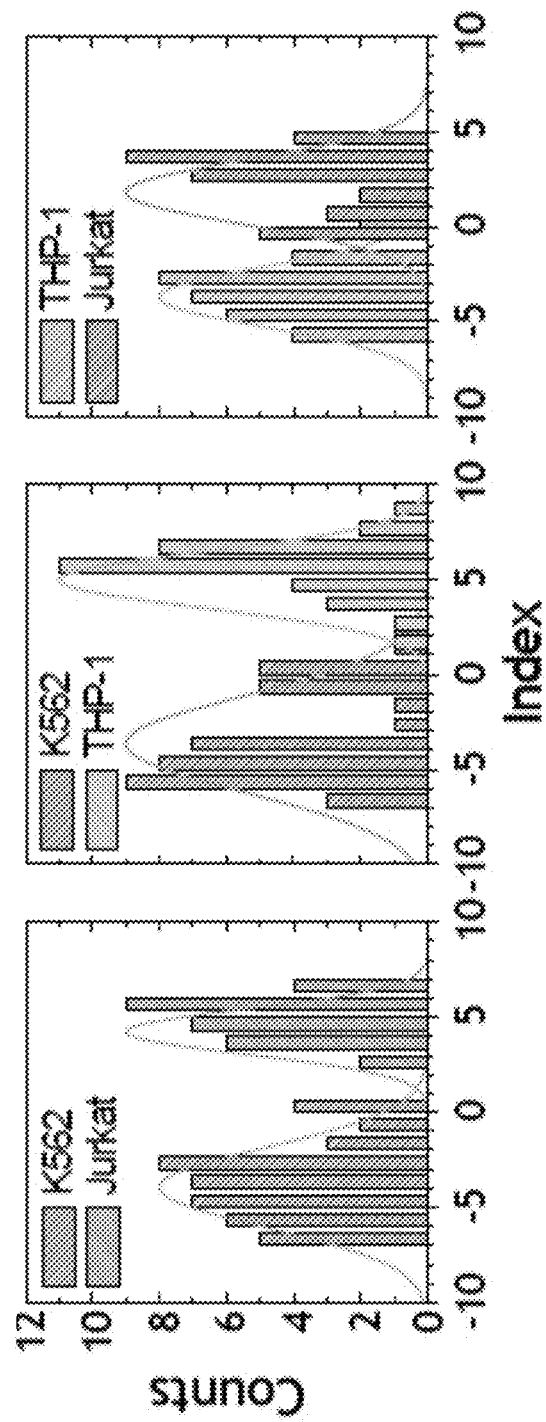
FIG. 8A
FIG. 8B
FIG. 8C
FIG. 8D

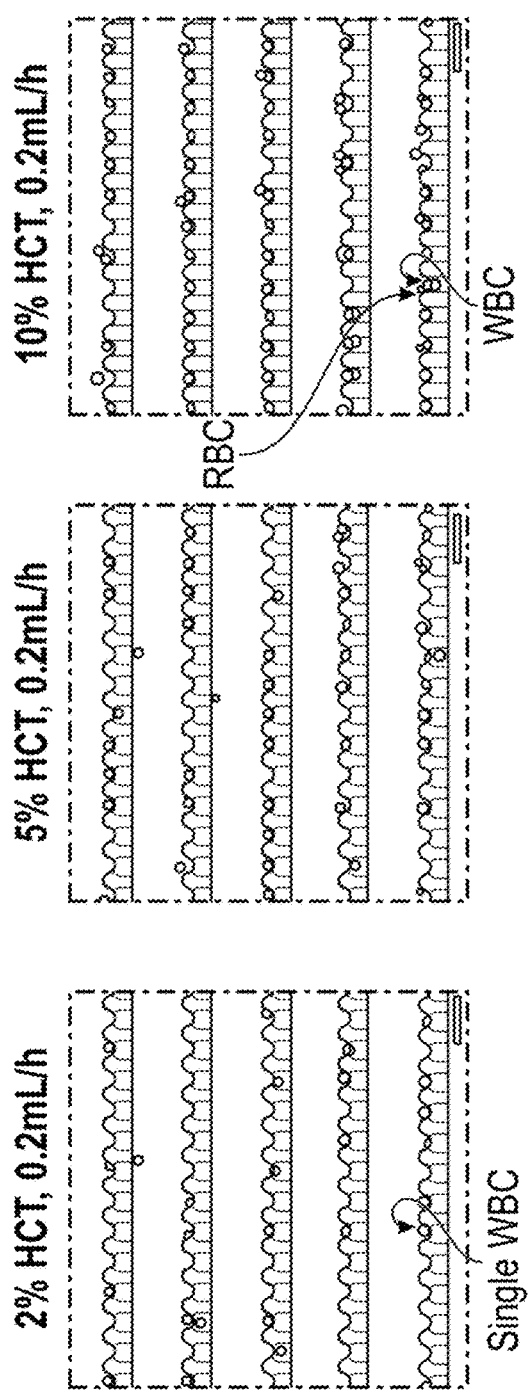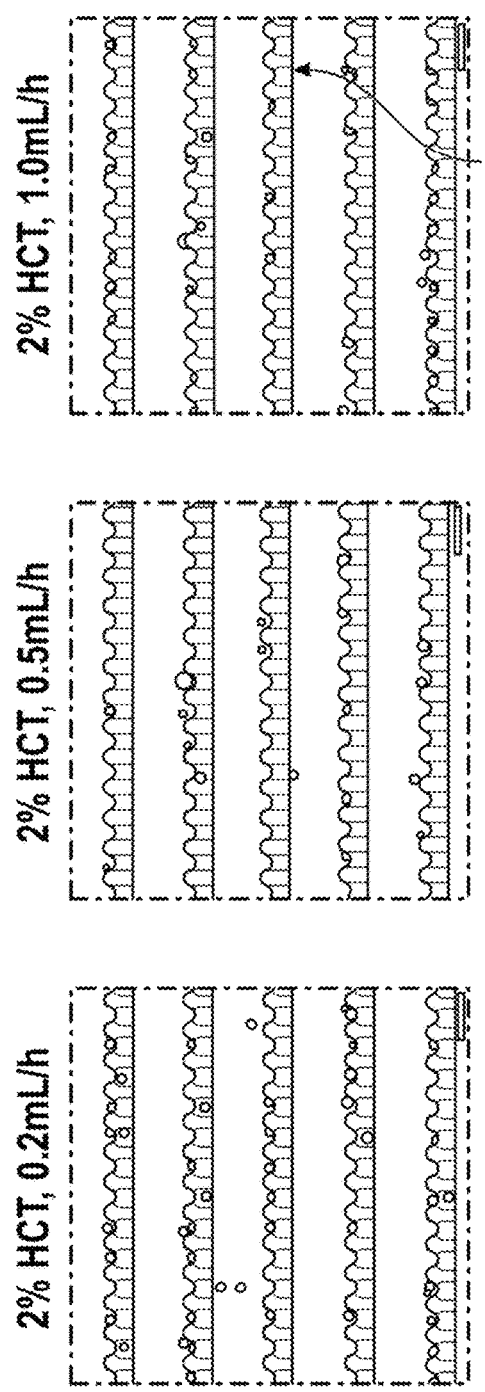

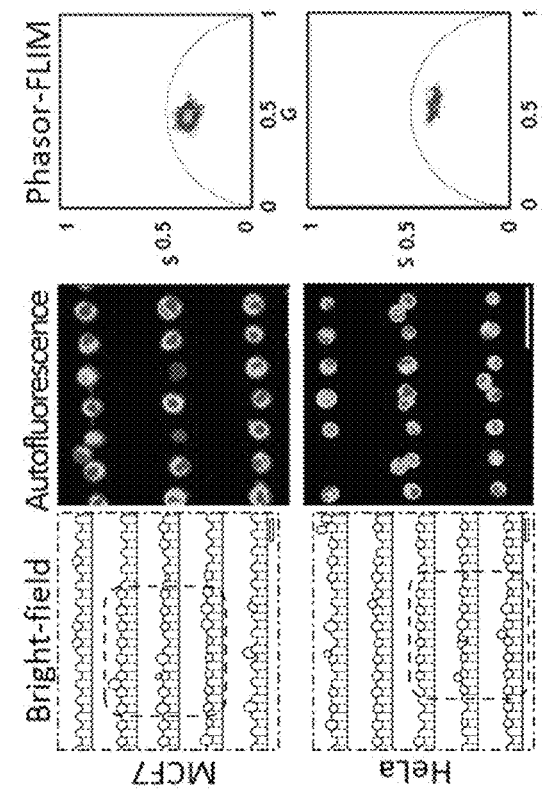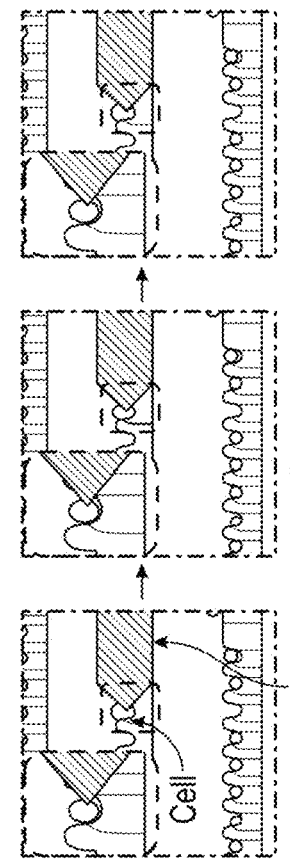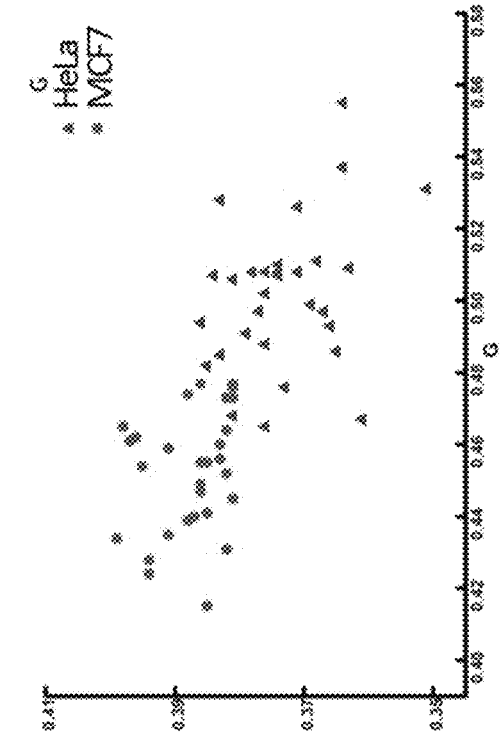
FIG. 13A
FIG. 13B
FIG. 13C
FIG. 13D
FIG. 13E

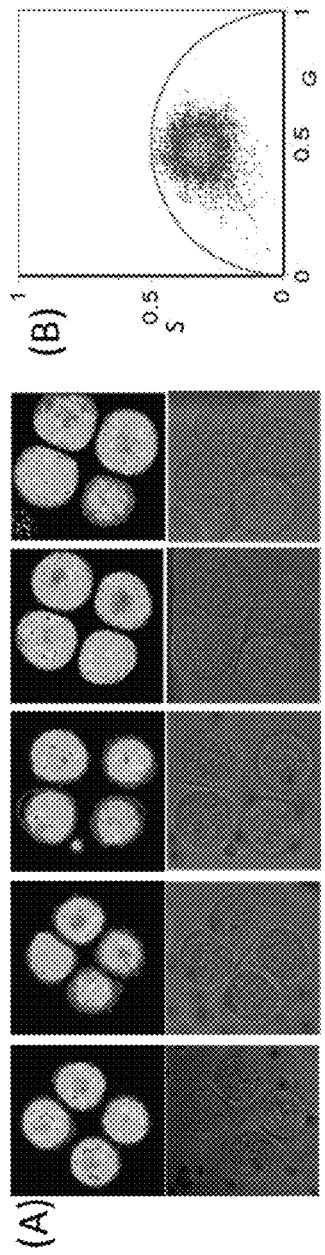
FIG. 14A
FIG. 14B
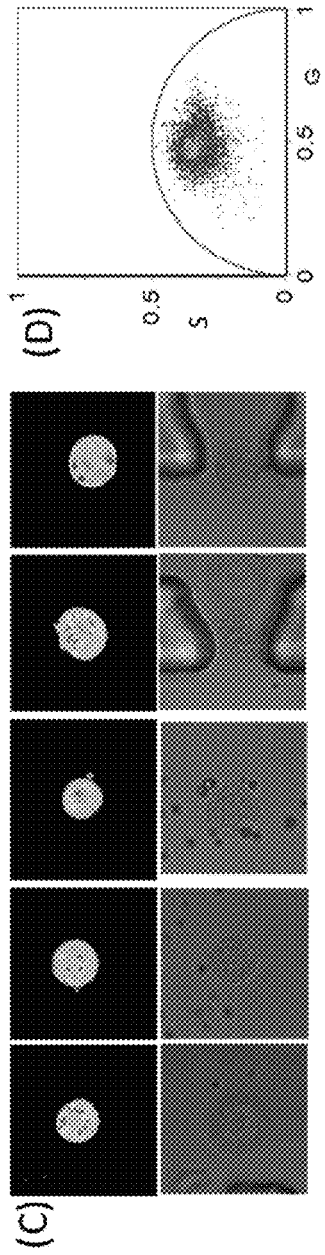
FIG. 14C
FIG. 14D
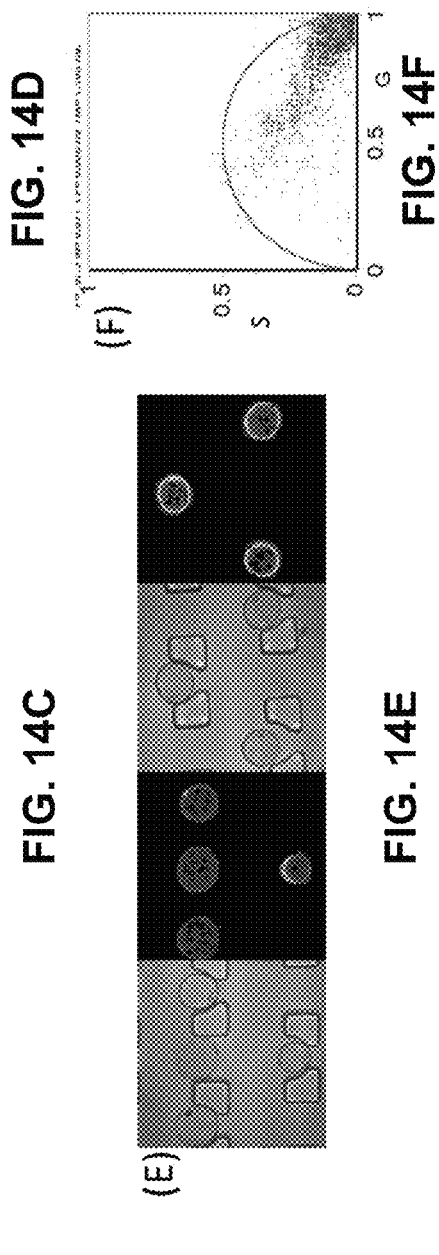
FIG. 14E
FIG. 14F

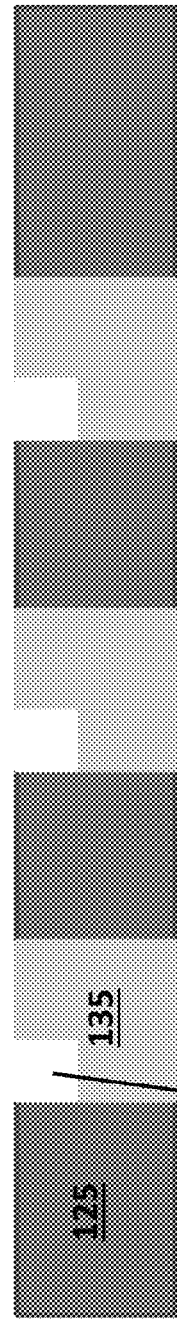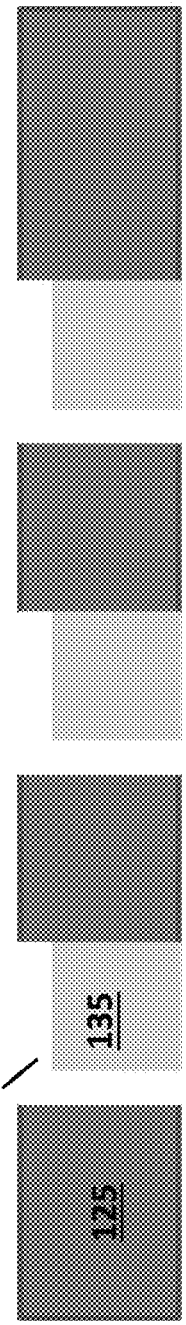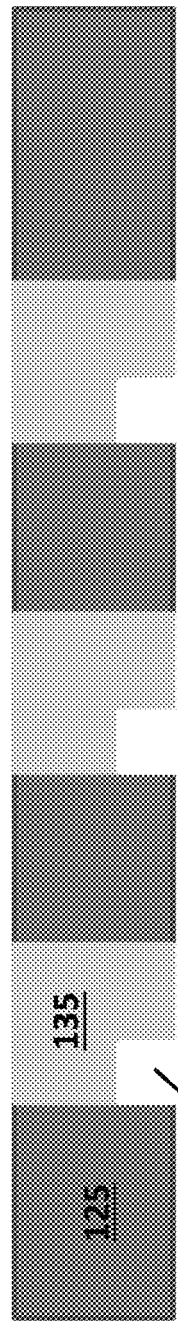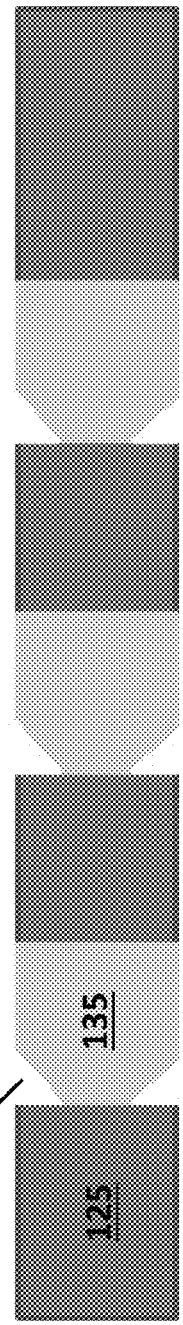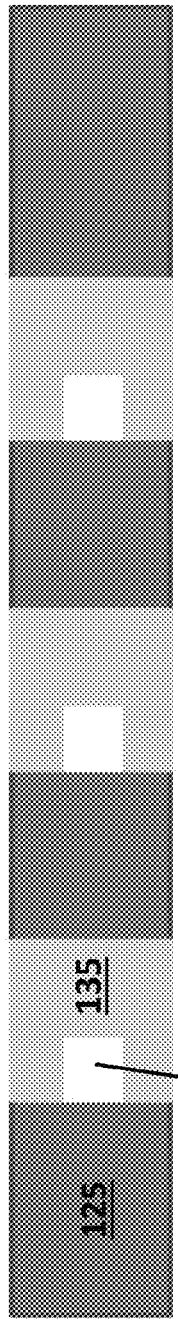

MICROFLUIDIC LABEL-FREE ISOLATION AND IDENTIFICATION OF CELLS USING FLUORESCENCE LIFETIME IMAGING (FLIM)

CROSS REFERENCE

This application is a continuation-in-part and claims priority to PCT Application No. PCT/US2018/055722 filed Oct. 12, 2018, which claims priority to U.S. Provisional Patent Application No. 62/571,746, filed Oct. 12, 2017, the specifications of which are incorporated herein in their entirety by reference.

GOVERNMENT SUPPORT

This invention was made with government support under Grant No. IIP-1538813 awarded by the National Science Foundation. The government has certain rights in the invention.

FIELD OF THE INVENTION

The present invention relates to methods and devices for isolating and identifying cells using fluorescence lifetime imaging (FLIM). More specifically, the methods and devices are microfluidic.

BACKGROUND OF THE INVENTION

Single-cell analysis is a growing practice within the field of microfluidics. It is often beneficial to be able to analyze individual cells instead of collecting average data on a population of cells. Methods which allow for high-throughput single-cell analysis are especially desirable. While some detection methods are destructive, non-destructive methods which leave the cells intact and viable for further analysis or culturing would be preferred.

Application of Microfluidic Single-Cell Analysis for Mammalian Cells:

Leukemia, a group of blood cancers that are characterized by the uncontrolled production and result in high numbers of abnormal leukocytes from the bone marrow, is the most prevalent pediatric cancer, and the sixth most common cause of cancer deaths in the U.S. Currently, bone marrow aspiration, and bone marrow biopsy has been used commonly as the standardized procedures for the diagnosis of leukemia and other blood disorders, however, these methods are usually invasive, risky, and difficult to acquire repeatedly over an extended time period. However, the blood-based detection such as complete blood count (CBC) and peripheral blood smear is gentle but cannot specify leukemia types; while selective biomarker immunostaining and cytogenetic analysis can determine the specific types of leukemia, but the whole procedures are complicated, time-consuming, and expensive. Therefore, the non-invasive and rapid isolation of single migratory leukemia cells with high sensitivity from unprocessed patient blood samples are therefore of crucial in leukemia diagnostics.

In terms of blood processing, microfluidic technology is a powerful tool to process blood sample and isolate circulating tumor cells (CTC) and leukemia cells in a high-throughput, low cost, and portable manner. In fact, a variety of high-performance microfluidic platforms have been established for isolation and enrichment of CTCs from blood as liquid biopsy, including inertial separation, surface acoustic waves, dielectrophoretic sorting and deterministic chromatography. These techniques are particularly powerful when CTCs have obviously larger diameter than white blood cells (WBC). However, in case of separation of leukemia cells from blood, the low purity of recovered leukemia cells remains a significant challenge because the size of leukemia cells may exhibit overlap with the size of leukocytes. One approach to improve the selectivity is deformability-based microfluidic discrimination of cancer cells, which results in higher-performance cancer cell capture from background cells despite their approximately identical size. In these approaches, however, the strong deformations may damage certain cancer cells due to the high shear stress, and the separation of cells through microstructured constrictions is limited by clogging, which reduces selectivity of cancer cells. Alternatively, cancer cells can be sorted based on epithelial cell surface markers expressed predominantly on cancer cells, such as epithelial cell adhesion molecule (EpCAM). However, the capture efficiency would be heavily dependent on the EpCAM expression level of cancer types and patients. In addition, recovery of biomarker-conjugated cells from the antibody-coated surface induces leukemia cell damage and requires an additional non-trivial step for culture and enumeration, Jackson and Li et al. separated the peripheral blood to search for circulating leukemic cells and lymphoblasts within the antibody-immobilized microfluidic channel, respectively, but still, need time-consuming labeling process and have typically yielded low sample purities (<1%), causing challenges in downstream analysis.

To overcome these difficulties beyond the enumeration of leukemia cells, the development of label-free technologies to identify and discriminate leukemia cells at a single-cell level has become critical for leukemia studies. The intrinsic auto-fluorescence of cells generated from endogenous proteins and metabolites is an alternative way to discriminate the cancer cells from normal differentiated cells. The widespread adoption of multiphoton fluorescence imaging and microscopy has followed progressive improvements in label-free and non-invasive detection of cellular metabolism and functional analysis with minimal photo-damage and maximized resolution. For example, nicotinamide adenine dinucleotide (NADH) is one of the main autofluorescent metabolic coenzymes involved in oxidative phosphorylation (OXPHOS) and glycolysis, reporting metabolic changes associated with cell carcinogenesis and differentiation. Based on the Warburg effect, tumor cells exhibit increased production of lactate because of a higher increased rate of glycolysis, in which a large population of free NADH is reproduced instead of a protein-bound form of NADH during electron transferring in OXPHOS. Thus, the ratio of free/bound NADH lower compared to that in tumor cells. Therefore, label-free, rapid, and noninvasive methods to measure cellular metabolic states and free/bound NADH levels of single leukemia cells are highly desirable to separate and detect of single leukemia cells from blood cells for biomedical applications.

Since different fluorophores (e.g. free versus protein-bound forms of NADH) have their specific fluorescence decay time and independent of their concentration, single leukemia cells can be discriminated based on by their fluorescence lifetime using a fluorescence lifetime imaging microscopy (FLIM). A phasor approach (phasor-FLIM) has been established for fluorescence lifetime data analysis allowing straightforward interpretation of intrinsic fluorescence signals from live tissues directly in terms of physiological relevant fluorophores. Each cell has its own signature on the phasor plot, corresponding to its metabolic patterns and the relative concentration of metabolites. Phasor-FLIM is a label-free and fit-free sensitive method to identify metabolic states of cells and can be used to classify stems cells, normal differentiated cells and cancer cells both in vitro and in a live tissue.

Application of Microfluidic Single-Cell Analysis for Plant Cells:

Single-cell analysis of plant cells is of critical importance in revealing the heterogeneity and unique characteristics of individual cells among the cell population. Microfluidic technology has been developed over the years to handle and isolate individual cells in a high-throughput manner. Furthermore, the rapid and reliable discrimination of the healthiness of single plant cells is also essential. Nowadays, with the increase in human population, the rapid and efficient breeding technologies are important for the development of improved cultivars by plant breeders. The doubled haploid (DH) technology enables line development with generating completely homozygous lines in a single step which is elementary to modern genetics and breeding approaches. During the past decades, the routine screening method was dominated by the inherited marker gene system which is very labor-intensive. To improve the screening system in an effective, accurate manner, the development of a novel system to identify the haploid and diploid seeds are important.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features high-throughput, single-cell analysis methods and devices which utilize microfluidic traps and FLIM detection to provide a non-destructive means of identifying and characterizing cells of interest within a population of cells.

One example is an automated new CTC identification method that combines passive hydrodynamic control for separation and trapping single living cancer cells in a continuous flow with the measurements of the time decay characteristics of cell's intrinsic autofluorescence through fluorescence lifetime Imaging microscopy (FLIM), a label-free and non-invasive approach to characterize the metabolic states of cells and tissues. In particular, FLIM allows a straightforward and label-free detection of intrinsic fluorescence signal from living cells at low magnification in terms of physiological relevant fluorophores. A phasor approach (phasor-FLIM) has been established for fluorescence lifetime data analysis allowing straightforward interpretation of intrinsic fluorescence signals from live tissues directly in terms of physiological relevant fluorophores. The combined deterministic single-cell trap array represents a novel method of size-based cell separation, enabling effective single-cell capture, easy measurements of time-integrated fluorescence intensity through FLIM, and highly scalable parallelization in a passive hydrodynamic device. With phasor FLIM measurement, cancer cells including MCF-7 and HeLa cells exhibit significantly different metabolic fingerprints compared to the WBCs, which allows an unbiased Identification and classification of metabolic states of cells without any labels in a similar way to flow cytometry scattergrams. It was also found that the FLIM signature of red blood cells could be distinguished obviously from the white blood cells and cancer cells within the microfluidic trapping arrays. It is believed that the label-free FLIM-based identification of single cancer cells based on the deterministic single-cell trap array could represent a promising tool for detecting and quantifying cancer cells from human blood, which could also be useful for clinical applications Including point-of-care diagnostics and cell-based therapeutics In biological laboratories.

A second example is a new single-plant-cell platform that combines passive hydrodynamic control for separation and trapping single plant cells from debris in a continuous flow with the measurements of the decay time characteristics of cell's intrinsic fluorescence through fluorescence lifetime imaging microscopy (FLIM), a label-free and non-invasive approach to characterize the intrinsic fluorescence biomarkers which has be used to indicate metabolic states of cells and tissues. In particular, FLIM allows a straightforward and label-free detection of the intrinsic fluorescence signal from living cells at low magnification in in terms of physiological relevant fluorophores. A phasor approach (phasor-FLIM) has been established for fluorescence lifetime data analysis allowing straightforward interpretation of intrinsic fluorescence signals from live tissues directly in terms of physiological relevant fluorophores. In the phasor-FLIM, each endogenous fluorescent can be distinguished by its distinct location in the phasor plot. Each cell has its own signature on the phasor plot, corresponding to its metabolic patterns and the relative concentration of intrinsic fluorescent metabolites. Phasor-FLIM is a label-free, fit-free and sensitive method to identify metabolic characteristics of cells and can be used to classify stems cells, normal differentiated cells and cancer cells both in vitro and in a live tissue. The device of the present invention can be used to isolate single plant cells and shows the capability to distinguish between healthy and unhealthy plant cells.

Maize microspore size can be used as a proxy for developmental stage or cell health. Size exclusion would be used as a means of pre-selecting from a mixed population to minimize non-target cells and debris within the FLIM device. Throughout development, maize microspores diameter can range from approximately 30 um to over 125 um. By using specific trap sizes and channel depths, specific microspore stages could be targeted. For example, microspores between 70-100 um may be pre-selected via size exclusion, trapped and analyzed using the FLIM device, then cultured.

Additionally, size exclusion could be important for targeting and standardizing the conformation of single protoplasts and walled single cells. Both cell types may form multicellular clumps which could interfere with downstream applications. By targeting cells in the 10-40 um range, large clusters and debris could be omitted from FLIM analysis and subsequent culturing.

One of the unique and inventive technical features of the present invention is the isolation and immobilization of selected cells in an array of microfluidic traps. Without wishing to limit the invention to any theory or mechanism, it is believed that the technical feature of the present invention advantageously provides for high-throughput single-cell FLIM analysis which is non-destructive and leaves the cells viable for culturing or further analysis. None of the presently known prior references or work has the unique inventive technical feature of the present invention.

Another key feature of the present invention is the use of single cell traps which have a pattern of gaps through the trap walls, which is asymmetric along a flow direction, for fluid and small components to pass through. Without wishing to limit the present invention to any particular theory or mechanism, this asymmetry is believed to result in a fluid flow through the gaps, which is asymmetric between the upstream trap edge and the downstream trap edge. This asymmetric fluid flow may provide for better trapping of large or less-deformable cells (such as plant cells) which could be difficult to capture with cells which have an asymmetric gap pattern.

When a cell interacts with a cell trap positioned along the side of a flow channel, the cell may not completely seat within the trap as it is moved down the channel past the trap. The partially trapped cell may then collide with the downstream edge of the cell trap. While a small, round, or more deformable cell might be deformed by this collision, and still be pulled into the trap, a large, less-deformable, or non-circular cell (such as a plant cell) may rigidly collide with the downstream edge and be rotated out of the trap by the passing fluid flow. As such, it may be considerably more difficult to trap small, round, more deformable cells than large, less-deformable, non-circular cells.

By designing the traps to have an asymmetric gap pattern, the traps may have a much greater pulling force (due to perpendicular flow through the gaps) at the upstream portion of the trap as compared to the downstream portion of the trap. This focusing of the pulling force may serve to capture the passing cells as soon as they pass the upstream edge of the trap by rotating them into the trap and holding them away from the downstream edge of the trap so as to avoid collision. This concentrated force may quickly tuck the entire cell within the trap, away from the influence of the fluid passing through the channel flow. If the perpendicular flow through the gap is very strong, the cell may be held against the upstream edge of the trap and completely prevented from touching the downstream edge of the trap. Alternatively, the perpendicular flow through the gap may be strong enough to quickly rotate the cell into the trap but not so strong as to prevent the cell from then repositioning within the trap so as to touch the downstream edge of the trap. In some embodiments, entry of the cell within the trap may decrease the perpendicular flow through the gaps such that the pulling force drops, and the cell is allowed to reposition within the trap against the downstream edge. In embodiments where the trapped cell rests against the downstream trap edge, flow of fluid and smaller components through the gaps may be substantially unhindered.

The gap pattern may be either symmetric or asymmetric in both the vertical and horizontal directions, and may be used to pin the cells differently depending on the application. In one embodiment for filtering, the gap pattern may be designed so that large cells are pinned to one side (either upstream or downstream side) of the trap and leave the other side unobstructed so as to allow for smaller cells to drain through the trap. In another embodiment, the gap pattern may be designed so as to pin cells centered in the trap so that drainage can occur on one or both sides of the trapped cell.

BRIEF DESCRIPTION OF THE DRAWINGS

The patent application or application file contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIGS. 1A-1L show a microfluidic platform of the present invention for the label-free Isolation and Identification of single cancer cells based on FLIM. FIG. 1A shows a schematic illustration of the microfluidic platform comprising the hydrodynamic filters and the array of single-cell traps and observation intrinsic single cell signal via FLIM. FIG. 1B shows a schematic of the microfluidic single-cell trapping region, in which white blood cells and cancer cells are trapped in the array individually, while red blood cells are passed through the trap and filtered out at the outlet chamber. FIG. 1C shows a schematic figure representing how different height gap areas affect the capturing of single WBCs and cancer cells and the filtering of RBCs. FIG. 1D shows a schematic drawing of a top view of the microfluidic device which illustrates both the channel flow and the perpendicular flow. FIG. 1E shows a schematic drawing of a side view of the microfluidic device which illustrates the height gaps at the top of the trap walls. FIG. 1F shows a schematic drawing of a side view of the microfluidic device which illustrates the height gaps at the bottom of the trap walls. FIG. 1G shows a schematic drawing of a side view of the microfluidic device which illustrates the height gaps at the top and bottom of the trap walls. FIG. 1H shows a schematic drawing of a side view of the microfluidic device which illustrates the gaps at the side of the trap walls. FIG. 1I shows a schematic drawing of a side view of the microfluidic device which illustrates the gaps at the corners of the trap walls. FIG. 1J shows a schematic drawing of a side view of the microfluidic device which illustrates the gaps at the top of the trap walls. FIG. 1K shows a schematic drawing of a side view of the microfluidic device which illustrates the gaps at the top and center of the trap walls. FIG. 1L shows a schematic drawing of a side view of the microfluidic device which illustrates the gaps at the corners of the trap walls.

FIGS. 2A-2H illustrate the trapping efficiency of the microfluidic device of the present invention under various operational conditions, FIG. 2A shows a bright-field microscope image illustrating the effect of 2% hematocrit and 0.2 mL/h input flow rate. FIG. 2B shows a bright-field microscope image illustrating the effect of 5% hematocrit and 0.2 mL/h input flow rate. FIG. 2C shows a bright-field microscope image illustrating the effect of 10% hematocrit and 0.2 mL/h input flow rate, FIG. 2D shows a plot illustrating single-cell trapping and multiple-cell occupancy for varying hematocrits. FIG. 2E shows a bright-field microscope image illustrating the effect of 2% hematocrit and 0.2 mL/h input flow rate. FIG. 2F shows a bright-field microscope image illustrating the effect of 2% hematocrit and 0.5 mL/h input flow rate. FIG. 2G shows a bright-field microscope image illustrating the effect of 2% hematocrit and 1.0 mL/h input flow rate. FIG. 2H shows a plot illustrating the percentage of trapped intact and deformed single and multiple WBCs for varying flow rates.

FIG. 3A shows a bright-field image of trapped single WBCs, MCF-7 and HeLa cells. FIG. 3B shows a magnified bright-field image of trapped single WBCs, MCF-7 and HeLa cells. FIG. 3C shows a magnified FLIM map of trapped single WBCs, MCF-7 and HeLa cells. FIG. 3D shows a magnified FLIM phasor plot with cursors representing the trapped WBCs, MCF-7 and HeLa cells. FIG. 3E shows a scatter plot showing the average phasors for the three different types of cells.

FIGS. 4A-4E show discrimination of single WBCs and RBCs based on the label-free FLIM measurement FIG. 4A shows a bright-field image of trapped single WBCs, RBCs, and MCF-7 cells. FIG. 4B shows a fluorescence intensity image of trapped single WBCs, RBCs, and MCF-7 cells. FIG. 4C shows a FLIM map of trapped single WBCs. RBCs, and MCF-7 cells. FIG. 4D shows a FLIM phasor plot with cursors representing the WBCs, RBCs, and MCF-7 cells. FIG. 4E shows a scatter plot showing the average phasors for the three different types of cells.

FIGS. 5A-5C show a microfluidic platform for the label-free isolation and rapid identification of single leukemia cells from blood based on FLIM. FIG. 5A shows a schematic illustration of the microfluidic platform comprising the hydrodynamic filters and the array of single-cell traps and observation intrinsic single cell signal via FLIM. FIG. 5B shows a schematic of the microfluidic single-cell trapping region, in which white blood cells and leukemia cells are trapped in the array individually, while red blood cells are passed through the trap and filtered out at the outlet chamber. FIG. 5C shows a schematic figure representing that different height gap areas affect the capturing of single WBCs and leukemia cells and filtering of RBCs.

FIG. 6A shows a histogram of the single-cell diameter of WBCs, THP-1, Jurkat, and K562 cells showing the overlap of cell diameter among the WBCs and leukemia cells. FIG. 6B shows the percentage of single-cell occupied traps according to different height gap areas (hg) of 0, 1.9, 3.3 and 5.5 µm, respectively. FIG. 6C shows a bright-field microscopic image of trapped single WBCs with 2% hematocrit at 0.2 mL/h input flow rate. Scale bar: 50 µm. FIG. 6D shows a bright-field microscopic image of trapped single WBCs with the flow off, after PBS washing. FIG. 6E shows a plot showing trap single-cell and multiple-cell occupancy for varying hematocrits. FIG. 6F shows a plot showing the percentage of trapped intact single, deformed single and multiple WBCs according to the input flow rate.

FIGS. 7A-7E show high-density single-cell trapping and heterogeneous phasor-FLIM signatures of different cell types. Scale bars: 50 µm. FIG. 7A shows (i) 40× bright-field images, (ii) magnified images of the selected regions of interest (ROI), (iii) NADH autofluorescence emission intensity images, and (iv) and corresponding lifetime phasor plots of the single-cell arrays of WBCs. FIG. 7B shows (i) 40× bright-field images, (ii) magnified images of the selected regions of interest (ROL), (iii) NADH autofluorescence emission intensity images, and (iv) and corresponding lifetime phasor plots of the single-cell arrays of THP-1 cells. FIG. 7C shows (i) 40× bright-field images, (ii) magnified images of the selected regions of interest (ROI), (iii) NADH autofluorescence emission intensity images, and (iv) and corresponding lifetime phasor plots of the single-cell arrays of Jurkat cells. FIG. 7D shows (i) 40× bright-field images, (ii) magnified images of the selected regions of interest (ROI), (iii) NADH autofluorescence emission intensity images, and (iv) and corresponding lifetime phasor plots of the single-cell arrays of K562 cells. FIG. 7E shows a scatter plot of the average g and s phasor values of trapped single cells based on their NADH autofluorescence phasor-FLIM signature. A total number of 65 WBCs, 35 THP-1 cells, 35 Jurkat cells, and 46 K562 cells are measured and plotted. While the heterogeneity between individual cells among the sample population is observed, all the leukemia cells shifts toward the right compared to WBCs, indicating a higher free-to-bound NADH ratio and a more glycolytic state.

FIGS. 8A-8D show the Separation of WBCs and different types of leukemia cells using multiparametric approach. The SI histograms were plotted based on the number of cell counts against separation index. The separation indexes have values from −10 to +10. FIG. BA shows a Separation index (SI) histogram of WBCs and the combined leukemia cell population of THP-1, Jurkat, and K562 cells. FIG. 8B shows a SI histogram of K562 versus Jurkat cells. FIG. 8C shows a SI histogram of K562 versus THP-1 cells. FIG. 6D shows a SI histogram of THP-1 versus Jurkat cells.

FIG. 9A shows bright-field images (i), NADH autofluorescence emission intensity images (ii), and NADH lifetime maps of leukemia cell-spiked blood samples (iii) of THP-1 cells. FIG. 9B shows bright-field images (i), NADH autofluorescence emission intensity images (ii), and NADH lifetime maps of leukemia cell-spiked blood samples (iii) of Jurkat cells. FIG. 9C shows bright-field images (i), NADH autofluorescence emission intensity images (ii), and NADH lifetime maps of leukemia cell-spiked blood samples (iii) of K562 cells. FIG. 9D shows a plot of the total phasor distribution of all the trapped single cells. FIG. 9E shows a linear increase of free to protein-bound NADH ratio, FIG. 9F shows a plot of NADH lifetime maps of leukemia cell-spiked blood samples. Leukemia cells demonstrate a significant shift toward a higher free/bound NADH ratio and shorter lifetime indicating a higher glycolytic state.

FIGS. 11A-11F show the highly efficient trapping of single leukemia cells and white blood cells in a high-density microwell array. FIG. 11A shows a bright-field microscope image illustrating the trapping of single cells with 2% hematocrit and 0.2 mL/h input flow rate. FIG. 11B shows a bright-field microscope image illustrating the trapping of single cells with 5% hematocrit and 0.2 mL/h input flow rate. FIG. 11C shows a bright-field microscope image illustrating the trapping of single cells with 10% hematocrit and 0.2 mL/h input flow rate. FIG. 11D shows a bright-field microscope image illustrating the trapping of single cells with 2% hematocrit and 0.2 mL/h input flow rate. FIG. 11E shows a bright-field microscope image illustrating the trapping of single cells with 2% hematocrit and 0.5 mL/h input flow rate. FIG. 11F shows a bright-field microscope image illustrating the trapping of single cells with 2% hematocrit and 1.0 mL/h input flow rate.

FIG. 13A shows a photograph of 100 single cells trapped in the ultra-thin PDMS membrane-sealed single-cell array. Scale bar: 100 µm, FIG. 13B shows bright-field images representing the single-cell mRNA probing process. The probe moved downward toward a target cell, penetrated through the membrane and inserted into the target cell to extract mRNAs by DEP. Scale bar: 30 µm.

FIG. 13C shows a gene expression heat map of trapped single MCF7 and U937 cells based on the RT-qPCR results of the probed-out mRNAs, FIG. 13D shows bright-field images, autofluorescence intensity images, and phasor-FLIM plots of MCF7 and HeLa single-cell arrays. Scale bar: 200 µm.

FIG. 13E shows a scatter plot of average phasor-FLIM values of individual HeLa and MCF7 cells in FIG. 13D.

FIG. 14A shows bright-field and auto-fluorescence intensity images of tetrad cells.

FIG. 14B shows a corresponding auto-fluorescence lifetime phasor plot of the tetrad cells of FIG. 14A.

FIG. 14C shows bright-field and auto-fluorescence intensity images of separated single plant cells.

FIG. 14D shows a corresponding auto-fluorescence lifetime phasor plot of the separated single plant cells of FIG. 14C.

FIG. 14E shows bright-field and auto-fluorescence intensity images of late uninucleate microspores.

FIG. 14F is a corresponding auto-fluorescence lifetime phasor plot of the microspores of FIG. 14E.

FIG. 15A shows bright-field and the corresponding FLIM images of healthy and unhealthy late uninucleate microspores, FIG. 15B shows an intrinsic fluorescence lifetime phasor plot of the separated single cells of FIG. 15A. The traps may also be designed to capture healthy cells and allow the unhealthy cells to pass through.

FIG. 16A shows a schematic illustration of the microfluidic platform comprising the hydrodynamic filters and the array of single-cell traps and observation intrinsic single cell signal via FLIM. FIG. 16B shows a schematic of the microfluidic single-cell trapping region, in which big plant cells (e.g. microspores) are trapped in the array individually, while debris is passed through the trap and filtered out at the outlet chamber.

FIG. 18A shows a schematic drawing of a side view of a microfluidic device having the height gaps at the top corners of the trap walls such that each trap has a gap pattern which is asymmetric along the flow direction. Note that the flow direction may be from either the right or the left, such that the flow is focused in either the upstream or the downstream portion of the trap.

FIG. 18B shows a schematic drawing of a side view of a microfluidic device having the height gaps at the top and edge of the trap walls such that each trap has a gap pattern which is asymmetric along the flow direction, Note that the flow direction may be from either the right or the left, such that the flow is focused in either the upstream or the downstream portion of the trap.

FIG. 18C shows a schematic drawing of a side view of a microfluidic device having the height gaps at the bottom corners of the trap walls such that each trap has a gap pattern which is asymmetric along the flow direction. Note that the flow direction may be from either the right or the left, such that the flow is focused in either the upstream or the downstream portion of the trap.

FIG. 18D shows a schematic drawing of a side view of a microfluidic device having the height gaps at the top and bottom corners of the trap walls such that each trap has a gap pattern which is asymmetric along the flow direction. Note that the flow direction may be from either the right or the left, such that the flow is focused in either the upstream or the downstream portion of the trap.

FIG. 18E shows a schematic drawing of a side view of a microfluidic device having the height gaps at the center of the edge of the trap walls such that each trap has a gap pattern which is asymmetric along the flow direction. Note that the flow direction may be from either the right or the left, such that the flow is focused in either the upstream or the downstream portion of the trap.

DESCRIPTION OF PREFERRED EMBODIMENTS

Figure 1B:
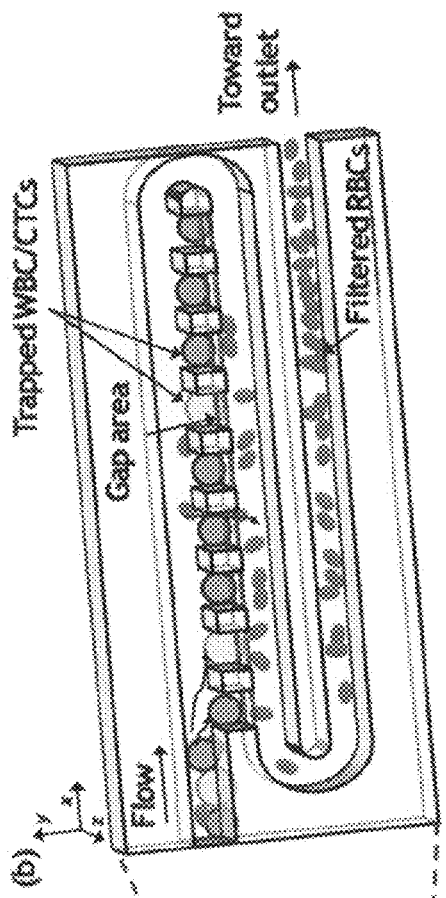

As used herein, "single cell" may refer to an individual animal, plant or bacteria cell, or to a single tetrad or microspore. As used herein, "microspore" may refer to a tetrad or a uninucleate microspore.

In one embodiment, the present invention features a high-throughput microfluidic system (100) for simultaneously sorting selected cells from a mixture and trapping the selected cells. As a non-limiting example, the system may comprise: a microfluidic device (110) comprising an inlet (112), an outlet (114), a top (116), a bottom (118), and a height between the top (116) and the bottom (118); a microfluidic channel (120) between the inlet (112) and the outlet (114) having a direction of fluid flow along the channel (120); a plurality of traps (130) along a side of the channel (120), each trap (130) being partially open to the channel (120) and partially bounded by a trap wall (135); and a plurality of gaps (140), each gap (140) passing through the trap wall (135), such that the trap wall (135) comprises a partial wall, and fluidly connecting an interior of a trap (130) with the outlet (114) via the channel (120), in another embodiment, the traps (130) may be configured to sort the mixture and trap selected cells while allowing fluid and the smaller components of the mixture to pass through the gaps (140) and the outlet (114) even when the trap contains a selected cell. In another embodiment, the channel may comprise one or more channel walls (125).

In another embodiment, the gaps (140) may comprise a height gap (140) large enough to allow for a fluid flow through the gap (140), and small enough that selected cells cannot pass through. In another embodiment, the gaps (140) may be are disposed along the tops, bottoms, sides, centers, or corners of the trap walls (135). In another embodiment, the gaps (140) may be elongated in shape. In another embodiment, the gaps (140) may be configured to allow the rest of the mixture to flow through the gap (140) even when the trap (130) holds a selected cell. In another embodiment, the channel (120) may comprise two or more traps (130) along a straight path.

In another embodiment, the system may comprise a selected cell and a plurality of smaller structures. In another embodiment, the gap (140) may comprise a shape, a size, and a position such that the gap (140) is not blocked when the trap (130) contains a selected cell, but rather allow fluid and the plurality of smaller structures to flow through. In another embodiment, the shape, size, and position of the gap (140) may be determined by a shape and a size of the trap wall (135).

In one embodiment, the present invention features a high-throughput microfluidic system (100) for simultaneously sorting selected cells from a mixture and trapping the selected cells. As a non-limiting example, the system may comprise: a microfluidic device (110) comprising an inlet (112), an outlet (114), a top (116), a bottom (118), and a height between the top (116) and the bottom (118); a microfluidic channel (120) between the inlet (112) and the outlet (114), having a direction of fluid flow along the channel (120); a plurality of traps (130) along a side of the channel (120); and a plurality of elongated gaps (140), each gap (140) fluidly connecting an interior of a trap (130) with the outlet (114) via the channel (120). In another embodiment, the traps (130) are configured to sort the mixture and trap selected cells while allowing the rest of the mixture to pass through the gaps (140) and the outlet (114).

In another embodiment, the traps (130) may comprise single-cell traps. In another embodiment, the channel (120) may comprise a serpentine channel. In another embodiment, the height between the top (116) and bottom (118) of the device (110) may be about 120 μm. In other embodiments the height between the top (116) and bottom (118) of the device (110) may be about 1, 5, 10, 20, 30, 40, 50, 60, 70, 80, 90, 100, 110, 130, 140, 150, 200, 300, 400 or 500 μm. In another embodiment, the elongated gaps (140) may have a height gap of about 10 μm. In other embodiments, the elongated gaps (140) may have a height gap of about 1, 2, 3, 4, 5, 6, 7, 8, 9, 12, 14, 14, 18, 20, 40, 60, 80, 100, 120, 150, 200, or 250 μm. In another embodiment, the gap may comprise about 1, 5, 10, 15, 20, 25, 30, 35, 40, 45, 50, 60, 70, 80, or 90 percent of the height of the channel (120). In another embodiment, the elongated gaps (140) may comprise a height gap large enough to allow for a fluid or other small structures to flow through the gap (140), and small enough that selected cells cannot pass through. In another embodiment, the traps may be designed to capture tetrads, while allowing uninucleate microspores to pass through the gap.

In another embodiment, the fluid flow through the gap (140) may be a perpendicular flow to the flow along the channel (120), and the perpendicular flow may be configured to direct cells into the traps (130). In another embodiment, the perpendicular flow may result in a low pressure which directs selected cells into the traps (130). For a non-limiting example, it may be that, the larger the gap (140), the higher the perpendicular flow, the lower the pressure within the trap (130), and the greater the force pulling cells into the trap.

In another embodiment, the traps (130) may have a width or length corresponding to the size of the selected cell. As a non-limiting examples, the size could refer to a length, width, or diameter of the selected cell. In another embodiment, the traps (130) may have a width or length that is about 1.5 times the size of the cell. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the cell. In another embodiment, the traps (130) may have a width or length that is about 75 μm. In other embodiments, the traps may have a width or length that is about 5, 10, 15, 20, 25, 30, 40, 50, 60, 70, 80, 90, 100, 150, 200, 250, or 500 μm.

In another embodiment, the elongated gaps (140) may be configured to allow fluid or the rest of the mixture to flow through the gap (140) even when the trap (130) holds a selected cell. In another embodiment, the channel (120) may comprise two or more traps (130) along a straight path. Without wishing to limit the present invention to any particular theory or mechanism, it is believed that increasing the number of traps increases the filtering and trapping capabilities of the microfluidic device and allows for higher throughput of single-cells.

In an embodiment, the present invention features a method of analyzing a sample. As a non-limiting example, the method may comprise: providing a microfluidic device comprising an analysis region at least partially enclosed by a membrane, the analysis region comprising an array of single-cell traps configured to trap cells from a biological sample, trapping a first group of cells from the biological sample in the trapping array while allowing a second group of cells from the biological sample to flow through the trapping array, wherein an average size of the first group of cells is different from an average size of the second group of cells; and imaging at least a portion of the trapping array with an imaging system.

In another embodiment, the imaging system may comprise fluorescence lifetime imaging microscopy (FLIM). In another embodiment, the FLIM may simultaneously image multiple immobilized cells. In another embodiment, a phasor plot may be used to analyze FLIM data. In another embodiment, FLIM data may be used to identify a metabolic pattern. In another embodiment, the method may further comprise identifying a first type of cells in the first group of cells based on measurements obtained by the imaging system. In another embodiment, the method may further comprise extracting cellular components from selected cells using an external micro-manipulating instrument configured to penetrate the membrane. In another embodiment, mRNA may be aspirated from selected imaged cells.

In another embodiment, the biological sample may comprise blood, the first group of cells may comprise white blood cells (WBCs) or circulating tumor cells (CTCs), and the second group of cells may comprise red blood cells (RBCs), In another embodiment, the first type of cells may comprise white blood cells (WBCs) or circulating tumor cells (CTCs). In another embodiment, the cells may comprise animal cells, plant cells, or bacteria cells. In another embodiment, the animal cells may comprise healthy cells, unhealthy cells, blood cells, red blood cells (RBCs), white blood cells (WBCs), cancer cells, or circulating tumor cells (CTCs). In another embodiment, the plant cells may comprise microspores in any developmental stage, tetrads, pollen grain cells, protoplasts, or cells with cell walls. In another embodiment, the microfluidic device may trap healthy cells and allow unhealthy cells to pass through. As a non-limiting example, "healthy cell" may be cells that are more viable than "unhealthy cells." In another embodiment, the microfluidic device may trap undesiccated cells and allow desiccated cells to pass through.

In another embodiment, the traps may be arranged along a serpentine channel. In another embodiment, the channel may have a height of about 120 μm. In other embodiments, the channel may have a height of about 1, 5, 10, 20, 30, 40, 50, 60, 70, 80, 90, 100, 110, 130, 140, 150, 200, 300, 400 or 500 μm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 μm. In other embodiments, the height gap may be about 1, 2, 3, 4, 5, 6, 7, 8, 9, 12, 14, 16, 18, 20, 40, 60, 80, 100, 120, 150, 200, or 250 μm. In another embodiment, the gap may comprise about 1, 5, 10, 15, 20, 25, 30, 35, 40, 45, 50, 60, 70, 80, or 90 percent of the height of the channel. In another embodiment, the height gap may be large enough to allow for a fluid flow through the gap, and small enough that the first group of cells cannot pass through. In another embodiment, the traps may be designed to capture tetrads, while allowing uninucleate microspores to pass through the gap.

In another embodiment, the fluid flow through the gap may be a perpendicular flow to a main channel flow, and the perpendicular flow may direct cells into the traps. In another embodiment, the perpendicular flow may result in a low pressure which directs cells into the traps. For a non-limiting example, it may be that, the larger the gap, the higher the perpendicular flow, the lower the pressure within the trap, and the greater the force pulling cells into the trap. In another embodiment, the gap allows fluid or the second group of cells to flow through the gap even when the trap holds a cell from the first group of cells.

In another embodiment, the traps (130) may have a width or length corresponding to the size of the selected cell. As a non-limiting examples, the size could refer to a length, width, or diameter of the selected cell. In another embodiment, the traps (130) may have a width or length that is about 1.5 times the size of the cell. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the cell. In another embodiment, the traps (130) may have a width or length that is about 75 μm. In other embodiments, the traps may have a width or length that is about 5, 10, 15, 20, 25, 30, 40, 50, 60, 70, 80, 90, 100, 150, 200, 250, or 500 μm.

In another embodiment, the method may be non-destructive, label free, or non-invasive. In another embodiment, the cells may be sorted before or after they are trapped. As a non-limiting example, the cells may be sorted by size exclusion, a hydrodynamic force, a dielectrophoresis force, a magnetic force, or an ultrasonic force. In another embodiment, debris may be blocked from the analysis region by a pillar array. In another embodiment, the cells may be selectively released from the traps or gated within the traps after analysis.

In another embodiment, the analysis region may comprise a transparent bottom or a glass bottom. In another embodiment, the analysis region may comprise a porous or nonporous membrane covering the top. In another embodiment, the imaged cells may be viable for further analysis or culturing. In another embodiment, selected cells may be cultured or further analyzed after imaging. In another embodiment, the cells may form a monolayer in the analysis region.

In an embodiment, the present invention features a method of single cell analysis. As a non-limiting example, the method may comprise: immobilizing a population of cells in a monolayer on a substrate in a microfluidic device; imaging the population of cells using FLIM; and analyzing the FLIM data of a single cell within the population.

In another embodiment, the FLIM may simultaneously image multiple immobilized cells. In another embodiment, a phasor plot may be used to analyze FLIM data. In another embodiment, FLIM data may be used to identify a metabolic pattern. In another embodiment, the method may further comprise extracting cellular components from selected cells using an external micro-manipulating instrument configured to penetrate the membrane. In another embodiment, mRNA may be aspirated from selected imaged cells.

In another embodiment, the cells may comprise animal cells, plant cells, or bacteria cells. In another embodiment, the animal cells may comprise healthy cells, unhealthy cells, blood cells, red blood cells (RBCs), white blood cells (WBCs), cancer cells, or circulating tumor cells (CTCs). In another embodiment, the plant cells may comprise microspores in any developmental stage, tetrads, pollen grain cells, protoplasts, or cells with cell walls.

In another embodiment, the cells may be immobilized using traps or chemical ligands. In another embodiment, the traps may selectively immobilize cells of a chosen size range. In another embodiment, the traps may be arranged along a serpentine channel. In another embodiment, the channel may have a height of about 120 μm. In other embodiments, the channel may have a height of about 1, 5, 10, 20, 30, 40, 50, 60, 70, 80, 90, 100, 110, 130, 140, 150, 200, 300, 400 or 500 μm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 μm. In other embodiments, the height gap may be about 1, 2, 3, 4, 5, 6, 7, 8, 9, 12, 14, 16, 18, 20, 40, 60, 80, 100, 120, 150, 200, or 250 μm. In another embodiment, the gap may comprise about 1, 5, 10, 15, 20, 25, 30, 35, 40, 45, 50, 60, 70, 80, or 90 percent of the height of the channel. In another embodiment, the height gap may be large enough to allow for a fluid flow through the gap, and small enough that the selected cells cannot pass through. In another embodiment, the traps may be designed to capture tetrads, while allowing uninucleate microspores to pass through the gap.

In another embodiment, the fluid flow through the gap may be a perpendicular flow to a main channel flow, and the perpendicular flow may direct cells into the traps. In another embodiment, the perpendicular flow may result in a low pressure which directs cells into the traps. For a non-limiting example, it may be that, the larger the gap, the higher the perpendicular flow, the lower the pressure within the trap, and the greater the force pulling cells into the trap. In another embodiment, the gap may allow fluid flow through the gap even when the trap holds a selected cell.

In another embodiment, the traps (130) may have a width or length corresponding to the size of the selected cell. As a non-limiting examples, the size could refer to a length, width, or diameter of the selected cell. In another embodiment, the traps (130) may have a width or length that is about 1.5 times the size of the cell. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the cell. In another embodiment, the traps (130) may have a width or length that is about 75 μm. In other embodiments, the traps may have a width or length that is about 5, 10, 15, 20, 25, 30, 40, 50, 60, 70, 80, 90, 100, 150, 200, 250, or 500 μm.

In another embodiment, the method may be non-destructive, label free, or non-invasive. In another embodiment, the cells may be sorted before or after they are immobilized. As a non-limiting example, the cells may be sorted by size exclusion, a hydrodynamic force, a dielectrophoresis force, a magnetic force, or an ultrasonic force. In another embodiment, debris may be blocked from the analysis region by a pillar array. In another embodiment, the cells may be selectively released from the traps or gated within the traps after analysis.

In another embodiment, the microfluidic device may comprise a transparent bottom or a glass bottom. In another embodiment, the microfluidic device may comprise a porous or nonporous membrane covering the top. In another embodiment, the imaged cells may be viable for further analysis or culturing. In another embodiment, selected cells may be cultured or further analyzed after imaging. In another embodiment, the cells may form a monolayer in the analysis region.

In an embodiment, the present invention features a method of sorting single cells based on FLIM, As a non-limiting example, the method may comprise: flowing a population of cells through a microfluidic device; imaging the cells using FLIM; analyzing each single cell within the population using the FLIM data; and sorting the analyzed cells based on the analysis.

In another embodiment, the FLIM may simultaneously image multiple cells. In another embodiment, a phasor plot may be used to analyze FLIM data. In another embodiment, FLIM data may be used to identify a metabolic pattern. In another embodiment, the method may further comprise extracting cellular components from selected cells using an external micro-manipulating instrument configured to penetrate the membrane. In another embodiment, mRNA may be aspirated from selected imaged cells.

In another embodiment, the cells may comprise animal cells, plant cells, or bacteria cells. As non-limiting examples, the animal cells may comprise healthy cells, unhealthy cells, blood cells, red blood cells (RBCs), white blood cells (WBCs), cancer cells, or circulating tumor cells (CTCs). As other non-limiting examples, the plant cells may comprise microspores in any developmental stage, tetrads, pollen grain cells, protoplasts, or cells with cell walls. In another embodiment, the cells may be immobilized during the FLIM. In another embodiment, the cells may be move slowly during the FLIM.

In another embodiment, the cells may be immobilized using traps or chemical ligands. In another embodiment, the traps may selectively immobilize cells of a chosen size range. For example, cells which are larger or smaller than the chosen size range may pass by or through the traps without being immobilized.

In another embodiment, the traps may be arranged along a serpentine channel. In another embodiment, the channel may have a height of about 120 rm. In other embodiments, the channel may have a height of about 1, 5, 10, 20, 30, 40, 50, 60, 70, 80, 90, 100, 110, 130, 140, 150, 200, 300, 400 or 500 µm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 um. In other embodiments, the height gap may be about 1, 2, 3, 4, 5, 6, 7, 8, 9, 12, 14, 16, 18, 20, 40, 60, 80, 100, 120, 150, 200, or 250 µm. In another embodiment, the gap may comprise about 1, 5, 10, 15, 20, 25, 30, 35, 40, 45, 50, 60, 70, 80, or 90 percent of the height of the channel. In another embodiment, the height gap may be large enough to allow for a fluid flow through the gap, and small enough that the selected cells cannot pass through. In another embodiment, the traps may be designed to capture tetrads, while allowing uninucleate microspores to pass through the gap.

In another embodiment, the fluid flow through the gap may be a perpendicular flow to a main channel flow, and the perpendicular flow may direct cells into the traps. In another embodiment, the perpendicular flow may result in a low pressure which directs cells into the traps. For a non-limiting example, it may be that, the larger the gap, the higher the perpendicular flow, the lower the pressure within the trap, and the greater the force pulling cells into the trap. In another embodiment, the gap may allow fluid or a plurality of smaller cells to flow through the gap even when the trap holds a selected cell.

In another embodiment, the traps (130) may have a width or length corresponding to the size of the selected cell. As a non-limiting examples, the size could refer to a length, width, or diameter of the selected cell. In another embodiment, the traps (130) may have a width or length that is about 1.5 times the size of the cell. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the cell. In another embodiment, the traps (130) may have a width or length that is about 75 µm. In other embodiments, the traps may have a width or length that is about 5, 10, 15, 20, 25, 30, 40, 50, 60, 70, 80, 90, 100, 150, 200, 250, or 500 µm.

In another embodiment, the method may be non-destructive, label free, or non-invasive. In another embodiment, the cells may be sorted before or after they are trapped. As a non-limiting example, the cells may be sorted by size exclusion, a hydrodynamic force, a dielectrophoresis force, a magnetic force, or an ultrasonic force. In another embodiment, debris may be blocked from the analysis region by a pillar array. In another embodiment, the cells may be selectively released from the traps or gated within the traps after analysis.

In another embodiment, the microfluidic device may comprise a transparent bottom or a glass bottom. In another embodiment, the microfluidic device may comprise a porous or nonporous membrane covering the top. In another embodiment, the sorted cells may be viable for further analysis or culturing. In another embodiment, selected cells may be cultured or further analyzed after sorting. In another embodiment, the cells may form a monolayer in the analysis region.

In an embodiment, the present invention features a method of identifying individual mammalian cells of interest using FLIM. As a non-limiting example, the method may comprise: immobilizing a population of mammalian cells in a monolayer on a substrate in a microfluidic device; imaging the cells using FLIM; and analyzing the FLIM data of a single cell within the population to identify if the cell is a cell of interest.

In another embodiment, the FLIM may simultaneously image multiple immobilized cells. In another embodiment, a phasor plot may be used to analyze FLIM data. In another embodiment, FLIM data may be used to identify a metabolic pattern. In another embodiment, the method may further comprise extracting cellular components from the cells of interest using an external micro-manipulating instrument configured to penetrate the membrane. In another embodiment, mRNA may be aspirated from selected imaged cells.

In another embodiment, the cells comprise healthy cells, unhealthy cells, blood cells, red blood cells (RBCs), white blood cells (WBCs), cancer cells, or circulating tumor cells (CTCs). In another embodiment, the cells may be immobilized using traps or chemical ligands. In another embodiment, the traps may selectively immobilize cells of a chosen size range.

In another embodiment, the traps may be arranged along a serpentine channel. In another embodiment, the channel may have a height of about 120 µm. In other embodiments, the channel may have a height of about 1, 5, 10, 20, 30, 40, 50, 60, 70, 80, 90, 100, 110, 130, 140, 150, 200, 300, 400 or 500 µm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 µm. In other embodiments, the height gap may be about 1, 2, 3, 4, 5, 6, 7, 8, 9, 12, 14, 16, 18, 20, 40, 60, 80, 100, 120, 150, 200, or 250 µm. In another embodiment, the gap may comprise about 1, 5, 10, 15, 20, 25, 30, 35, 40, 45, 50, 60, 70, 80, or 90 percent of the height of the channel. In another embodiment, the height gap may be large enough to allow for a fluid flow through the gap, and small enough that the selected cells cannot pass through.

In another embodiment, the fluid flow through the gap may be a perpendicular flow to a main channel flow, and the perpendicular flow may direct cells into the traps. In another embodiment, the perpendicular flow may result in a low pressure which directs cells into the traps. For a non-limiting example, it may be that, the larger the gap, the higher the perpendicular flow, the lower the pressure within the trap, and the greater the force pulling cells into the trap. In another embodiment, the gap allows fluid or a plurality of smaller cells to flow through the gap even when the trap holds a selected cell. Without wishing to limit the present invention to any particular theory or mechanism, it is believed that an elongated gap may allow for the trap to immobilize a selected cell without blocking the flow of fluid an smaller cells or structures through the gap.

In another embodiment, the traps (130) may have a width or length corresponding to the size of the selected cell. As a non-limiting examples, the size could refer to a length, width, or diameter of the selected cell. In another embodiment, the traps (130) may have a width or length that is about 1.5 times the size of the cell. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the cell. In another embodiment, the traps (130) may have a width or length that is about 75 µm. In other embodiments, the traps may have a width or length that is about 5, 10, 15, 20, 25, 30, 40, 50, 60, 70, 80, 90, 100, 150, 200, 250, or 500 µm.

In another embodiment, the method may be non-destructive, label free, or non-invasive. In another embodiment, the cells may be sorted before or after they are trapped. As a non-limiting example, the cells may be sorted by size exclusion, a hydrodynamic force, a dielectrophoresis force, a magnetic force, or an ultrasonic force. In another embodiment, debris may be blocked from the analysis region by a pillar array. In another embodiment, the cells may be selectively released from the traps or gated within the traps after analysis.

In another embodiment, the microfluidic device may comprise a transparent bottom or a glass bottom. In another embodiment, the microfluidic device may comprise a porous or nonporous membrane covering the top. In another embodiment, the imaged cells may be viable for further analysis or culturing. In another embodiment, selected cells may be cultured or further analyzed after imaging. In another embodiment, the cells may form a monolayer in the analysis region.

In an embodiment, the present invention features a method of culturing selected mammalian cells. As a non-limiting example, the method may comprise: immobilizing a population of mammalian cells in a monolayer on a substrate in a microfluidic device; imaging the cells using FLIM; analyzing each single cell within the population using the FLIM data; selecting a subset of the population based on the analysis; and culturing the selected subset of cells.

In another embodiment, the FLIM may simultaneously image multiple immobilized cells. In another embodiment, a phasor plot may be used to analyze FLIM data. In another embodiment, FLIM data may be used to identify a metabolic pattern. In another embodiment, the method may further comprise extracting cellular components from selected cells using an external micro-manipulating instrument configured to penetrate the membrane. In another embodiment, mRNA may be aspirated from selected imaged cells.

In another embodiment, the cells may comprise healthy cells, unhealthy cells, blood cells, red blood cells (RBCs), white blood cells (WBCs), cancer cells, or circulating tumor cells (CTCs). In another embodiment, the cells may be immobilized using traps or chemical ligands. In another embodiment, the traps may selectively immobilize cells of a chosen size range.

In another embodiment, the traps may be arranged along a serpentine channel. In another embodiment, the channel may have a height of about 120 µm. In other embodiments, the channel may have a height of about 1, 5, 10, 20, 30, 40, 50, 60, 70, 80, 90, 100, 110, 130, 140, 150, 200, 300, 400 or 500 µm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 µm. In other embodiments, the height gap may be about 1, 2, 3, 4, 5, 6, 7, 8, 9, 12, 14, 16, 18, 20, 40, 60, 80, 100, 120, 150, 200, or 250 µm. In another embodiment, the gap may comprise about 1, 5, 10, 15, 20, 25, 30, 35, 40, 45, 50, 60, 70, 80, or 90 percent of the height of the channel. In another embodiment, the height gap may be large enough to allow for a fluid flow through the gap, and small enough that the selected cells cannot pass through.

In another embodiment, the fluid flow through the gap may be a perpendicular flow to a main channel flow, and the perpendicular flow may direct cells into the traps. In another embodiment, the perpendicular flow may result in a low pressure which directs cells into the traps. For a non-limiting example, it may be that, the larger the gap, the higher the perpendicular flow, the lower the pressure within the trap, and the greater the force pulling cells into the trap. In another embodiment, the gap may allow fluid or a plurality of smaller cells to flow through the gap even when the trap holds a selected cell.

In another embodiment, the traps (130) may have a width or length corresponding to the size of the selected cell. As a non-limiting examples, the size could refer to a length, width, or diameter of the selected cell. In another embodiment, the traps (130) may have a width or length that is about 1.5 times the size of the cell. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the cell. In another embodiment, the traps (130) may have a width or length that is about 75 µm. In other embodiments, the traps may have a width or length that is about 5, 10, 15, 20, 25, 30, 40, 50, 60, 70, 80, 90, 100, 150, 200, 250, or 500 µm.

In another embodiment, the method may be non-destructive, label free, or non-invasive. In another embodiment, the cells may be sorted before or after they are trapped. As a non-limiting example, the cells may be sorted by size exclusion, a hydrodynamic force, a dielectrophoresis force, a magnetic force, or an ultrasonic force. In another embodiment, debris may be blocked from the analysis region by a pillar array. In another embodiment, the cells may be selectively released from the traps or gated within the traps after analysis.

In another embodiment, the microfluidic device may comprise a transparent bottom or a glass bottom. In another embodiment, the microfluidic device may comprise a porous or nonporous membrane covering the top. In another embodiment, the imaged cells may be viable for further analysis or culturing. In another embodiment, selected cells may be cultured or further analyzed after imaging. In another embodiment, the cells may form a monolayer in the analysis region.

In an embodiment, the present invention features a method of screening plant cells using FLIM. As a non-limiting example, the method may comprise: immobilizing a population of plant cells in a monolayer on a substrate in a microfluidic device; imaging the population of cells using fluorescence lifetime imaging microscopy (FLIM); and analyzing the FLIM data of a single cell or tetrad within the population to identify if the cell is healthy.

In another embodiment, the FLIM may simultaneously image multiple immobilized cells. In another embodiment, a phasor plot may be used to analyze FLIM data. In another embodiment, FLIM data may be used to identify a metabolic pattern. In another embodiment, the method may further comprise extracting cellular components from selected cells using an external micro-manipulating instrument configured to penetrate the membrane. In another embodiment, mRNA may be aspirated from selected imaged cells.

In another embodiment, the plant cells may comprise microspores in any developmental stage, tetrads, pollen grain cells, protoplasts, or cells with cell walls. In another embodiment, the cells may be immobilized using traps or chemical ligands. In another embodiment, the traps may selectively immobilize cells of a chosen size range. In another embodiment, a shape of the traps may be designed to match a shape of the cells.

In another embodiment, the traps may be arranged along a serpentine channel. In another embodiment, the channel may have a height of about 120 µm. In other embodiments, the channel may have a height of about 1, 5, 10, 20, 30, 40, 50, 60, 70, 80, 90, 100, 110, 130, 140, 150, 200, 300, 400 or 500 µm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 µm. In other embodiments, the height gap may be about 1, 2, 3, 4, 5, 6, 7, 8, 12, 14, 16, 18, 20, 40, 60, 80, 100, 120, 150, 200, or 250 µm. In another embodiment, the gap may comprise about 1, 5, 10, 15, 20, 25, 30, 35, 40, 45, 50, 60, 70, 80, or 90 percent of the height of the channel. In another embodiment, the height gap may be large enough to allow for a fluid flow through the gap, and small enough that the selected cells cannot pass through. In another embodiment, the traps may be designed to capture tetrads, while allowing uninucleate microspores to pass through the gap.

In another embodiment, the fluid flow through the gap may be a perpendicular flow to a main channel flow, and the perpendicular flow may direct cells into the traps. In another embodiment, the perpendicular flow may result in a low pressure which directs cells into the traps. For a non-limiting example, it may be that, the larger the gap, the higher the perpendicular flow, the lower the pressure within the trap, and the greater the force pulling cells into the trap. In another embodiment, the gap may allow fluid or a plurality of smaller cells to flow through the gap even when the trap holds a selected cell.

In another embodiment, the traps (130) may have a width or length corresponding to the size of the selected cell. As a non-limiting examples, the size could refer to a length, width, or diameter of the selected cell. In another embodiment, the traps (130) may have a width or length that is about 1.5 times the size of the cell. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the cell. In another embodiment, the traps (130) may have a width or length that is about 75 µm. In other embodiments, the traps may have a width or length that is about 5, 10, 15, 20, 25, 30, 40, 50, 60, 70, 80, 90, 100, 150, 200, 250, or 500 µm.

In another embodiment, the method may be non-destructive, label free, or non-invasive. In another embodiment, the cells may be sorted before or after they are trapped. As a non-limiting example, the cells may be sorted by size exclusion, a hydrodynamic force, a dielectrophoresis force, a magnetic force, or an ultrasonic force. In another embodiment, debris may be blocked from the analysis region by a pillar array. In another embodiment, the cells may be selectively released from the traps or gated within the traps after analysis.

In another embodiment, the microfluidic device may comprise a transparent bottom or a glass bottom. In another embodiment, the microfluidic device may comprise a porous or nonporous membrane covering the top. In another embodiment, the imaged cells may be viable for further analysis or culturing. In another embodiment, selected cells may be cultured or further analyzed after imaging. In another embodiment, the cells may form a monolayer in the analysis region.

In an embodiment, the present invention features a method of culturing selected microspores. As a non-limiting example, the method may comprise: immobilizing a population of microspores on a substrate within a microfluidic device; imaging the microspores using FLIM; analyzing each single microspore within the population using the FLIM data; selecting a subset of the population based on the analysis; and culturing the selected subset of microspores.

In another embodiment, the FLIM may simultaneously image multiple immobilized microspores. In another embodiment, a phasor plot may be used to analyze FLIM data. In another embodiment, FLIM data may be used to identify a metabolic pattern. In another embodiment, the method may further comprise extracting cellular components from selected microspores using an external micro-manipulating instrument configured to penetrate the membrane. In another embodiment, mRNA may be aspirated from selected imaged microspores.

In another embodiment, the microspores may comprise canola microspores or maize microspores. In another embodiment, the microspores may be immobilized using traps or chemical ligands. In another embodiment, the traps may selectively immobilize microspores of a chosen size range. In another embodiment, a shape of the traps may be designed to match a shape of the microspores.

In another embodiment, the traps may be arranged along a serpentine channel. In another embodiment, the channel may have a height of about 120 µm. In other embodiments, the channel may have a height of about 1, 5, 10, 20, 30, 40, 50, 60, 70, 80, 90, 100, 110, 130, 140, 150, 200, 300, 400 or 500 µm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 µm. In other embodiments, the height gap may be about 1, 2, 3, 4, 5, 6, 7, 8, 9, 12, 14, 16, 18, 20, 40, 60, 80, 100, 120, 150, 200, or 250 µm. In another embodiment, the gap may comprise about 1, 5, 10, 15, 20, 25, 30, 35, 40, 45, 50, 60, 70, 80, or 90 percent of the height of the channel. In another embodiment, the height gap may be large enough to allow for a fluid flow through the gap, and small enough that the selected microspores cannot pass through. In another embodiment, the traps may be designed to capture tetrads, while allowing uninucleate microspores to pass through the gap.

In another embodiment, the fluid flow through the gap may be a perpendicular flow to a main channel flow, and the perpendicular flow may direct microspores into the traps. In another embodiment, the perpendicular flow may result in a low pressure which directs microspores into the traps. For a non-limiting example, it may be that, the larger the gap, the higher the perpendicular flow, the lower the pressure within the trap, and the greater the force pulling microspores into the trap. In another embodiment, the perpendicular flow may result in a low pressure which directs microspores into the traps. In another embodiment, the gap may allow fluid or a plurality of smaller cells to flow through the gap even when the trap holds a selected microspore.

In another embodiment, the traps (130) may have a width or length corresponding to the size of the selected microspore. As a non-limiting examples, the size could refer to a length, width, or diameter of the selected microspore. In another embodiment, the traps (130) may have a width or length that is about 1.5 times the size of the microspore. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the microspore. In another embodiment, the traps (130) may have a width or length that is about 75 µm. In other embodiments, the traps (130) may have a width or length that is about 5, 10, 15, 20, 25, 30, 40, 50, 60, 70, 80, 90, 100, 150, 200, 250, or 500 µm.

In another embodiment, the method may be non-destructive, label free, or non-invasive. In another embodiment, the microspores may be sorted before or after they are trapped. As a non-limiting example, the microspores may be sorted by size exclusion, a hydrodynamic force, a dielectrophoresis force, a magnetic force, or an ultrasonic force. In another embodiment, debris may be blocked from the analysis region by a pillar array. In another embodiment, the microspores may be selectively released from the traps or gated within the traps after analysis.

In another embodiment, the microfluidic device may comprise a transparent bottom or a glass bottom. In another embodiment, the microfluidic device may comprise a porous or nonporous membrane covering the top. In another embodiment, the imaged microspores may be viable for further analysis or culturing. In another embodiment, selected microspores may be cultured or further analyzed after imaging. In another embodiment, the microspores may form a monolayer in the analysis region.

In an embodiment, the present invention features a method of analyzing selected microspores. As a non-limiting example, the method may comprise: immobilizing a population of microspores on a substrate within a microfluidic device; imaging the microspores using FLIM; analyzing each single microspore within the population using the FLIM data; selecting a subset of the population based on the analysis; and aspirating mRNA from the selected subset of microspores for further analysis.

In another embodiment, the FLIM may simultaneously image multiple immobilized microspores. In another embodiment, a phasor plot may be used to analyze FLIM data. In another embodiment, FLIM data may be used to identify a metabolic pattern.

In another embodiment, the microspores may comprise canola microspores or maize microspores. In another embodiment, the microspores may be immobilized using traps or chemical ligands. In another embodiment, the traps may selectively immobilize microspores of a chosen size range. In another embodiment, a shape of the traps may be designed to match a shape of the microspores.

In another embodiment, the traps may be arranged along a serpentine channel. In another embodiment, the channel may have a height of about 120 µm. In other embodiments, the channel may have a height of about 1, 5, 10, 20, 30, 40, 50, 60, 70, 80, 90, 100, 110, 130, 140, 150, 200, 300, 400 or 500 µm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 µm. In other embodiments, the height gap may be about 1, 2, 3, 4, 5, 6, 7, 8, 9, 12, 14, 16, 18, 20, 40, 60, 80, 100, 120, 150, 200, or 250 µm. In another embodiment, the gap may comprise about 1, 5, 10, 15, 20, 25, 30, 35, 40, 45, 50, 50, 60, 70, 80, or 90 percent of the height of the channel. In another embodiment, the height gap may be large enough to allow for a fluid flow through the gap, and small enough that the selected microspores cannot pass through. In another embodiment, the traps may be designed to capture tetrads, while allowing uninucleate microspores to pass through the gap.

In another embodiment, the fluid flow through the gap may be a perpendicular flow to a main channel flow, and the perpendicular flow may direct microspores into the traps. In another embodiment, the perpendicular flow may result in a low pressure which directs microspores into the traps. For a non-limiting example, it may be that, the larger the gap, the higher the perpendicular flow, the lower the pressure within the trap, and the greater the force pulling microspores into the trap. In another embodiment, the gap allows fluid or a plurality of smaller cells to flow through the gap even when the trap holds a selected microspore.

In another embodiment, the traps (130) may have a width or length corresponding to the size of the selected microspore. As a non-limiting examples, the size could refer to a length, width, or diameter of the selected microspore. In another embodiment, the traps (130) may have a width or length that is about 1.5 times the size of the cells. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the microspore. In another embodiment, the traps (130) may have a width or length that is about 75 µm. In other embodiments, the traps (130) may have a width or length that is about 5, 10, 15, 20, 25, 30, 40, 50, 60, 70, 80, 90, 100, 150, 200, 250, or 500 µm.

In another embodiment, the method may be non-destructive, label free, or non-invasive. In another embodiment, the microspores may be sorted before or after they are trapped. As a non-limiting example, the microspores may be sorted by size exclusion, a hydrodynamic force, a dielectrophoresis force, a magnetic force, or an ultrasonic force. In another embodiment, debris may be blocked from the analysis region by a pillar array. In another embodiment, the microspores may be selectively released from the traps or gated within the traps after analysis.

In another embodiment, the microfluidic device may comprise a transparent bottom or a glass bottom. In another embodiment, the microfluidic device may comprise a porous or nonporous membrane covering the top. In another embodiment, the microspores may form a monolayer in the analysis region.

In an embodiment, the present invention features a microfluidic device comprising: an analysis region, the analysis region including a microfluidic channel configured to trap cells of a biological sample; and an imaging system configured to image the trapped cells. In another embodiment, the imaging system may comprise fluorescence lifetime imaging microscopy (FLIM). In another embodiment, the FLIM may be configured to simultaneously images multiple cells.

In another embodiment, the biological sample may comprise blood, the first group of cells may be white blood cells (WBCs) or circulating tumor cells (CTCs) and the second group of cells may be red, blood cells (RBCs). In another embodiment, the cells may be animal cells, plant cells, or bacteria cells. As non-limiting examples, the animal cells may be healthy cells, unhealthy cells, blood cells, red blood cells (RBCs), white blood cells (WBCs), cancer cells, or circulating tumor cells (CTCs). As other non-limiting examples, the plant cells may comprise microspores in any developmental stage, tetrads, pollen grain cells, protoplasts, or cells with cell walls.

In another embodiment, the device may comprise traps configured to trap the cells. In another embodiment, the traps may be arranged along a serpentine channel. In another embodiment, the channel may have a height of about 120 µm. In other embodiments, the channel may have a height of about 1, 5, 10, 20, 30, 40, 50, 60, 70, 80, 90, 100, 110, 130, 140, 150, 200, 300, 400 or 500 µm. In another embodiment, the traps may each comprise a gap, resulting in a gap area or height gap (hg). In another embodiment, the height gap may be set by the height of a half-wall which forms a side of the trap. In another embodiment, the gap may be elongated in shape. In another embodiment, the height gap is about 10 um. In other embodiments, the height gap may be about 1, 2, 3, 4, 5, 6, 7, 8, 9, 12, 14, 16, 18, 20, 40, 60, 80, 100, 120, 150, 200, or 250 um. In another embodiment, the gap may comprise about 1, 5, 10, 15, 20, 25, 30, 35, 40, 45, 50, 60, 70, 80, or 90 percent of the height of the channel. In another embodiment, the height gap may be large enough to allow for a fluid flow through the gap, and small enough that the first group of cells cannot pass through. In another embodiment, the traps may be designed to capture tetrads, while allowing uninucleate microspores to pass through the gap.

In another embodiment, the fluid flow through the gap may be a perpendicular flow to a main channel flow, and the perpendicular flow may direct cells into the traps. In another embodiment, the perpendicular flow may result in a low pressure which directs cells into the traps. For a non-limiting example, it may be that, the larger the gap, the higher the perpendicular flow, the lower the pressure within the trap, and the greater the force pulling cells into the trap. In another embodiment, the gap may be configured to allow fluid or a plurality of smaller cells to flow through the gap even when the trap holds a selected cell.

In another embodiment, the traps (130) may have a width or length corresponding to the size of the selected cell. As a non-limiting examples, the size could refer to a length, width, or diameter of the selected cell. In another embodiment, the traps (130) may have a width or length that is about 1.5 times the size of the cell. In other embodiments, the traps (130) may have a width or length that is about 0.5, 0.6, 0.7, 0.8, 0.9 1, 1.1, 1.2, 1.3, 1.4, 1.6, 1.7, 1.8, 1.9 or 9 times the size of the cell. In another embodiment, the traps (130) may have a width or length that is about 75 µm. In other embodiments, the traps may have a width or length that is about 5, 10, 15, 20, 25, 30, 40, 50, 60, 70, 80, 90, 100, 150, 200, 250, or 500 µm.

In another embodiment, the device may be configured to sort the cells before or after they are trapped. As non-limiting examples, the device may be configured to sort the cells by size exclusion, a hydrodynamic force, a dielectrophoresis force, a magnetic force, or an ultrasonic force. In another embodiment, the device may comprise a pillar array configured to block debris from the analysis region. In another embodiment, the analysis region may comprise a transparent or a glass bottom. In another embodiment, the cells may form a monolayer in the analysis region.

In another embodiment, the device further comprises: a membrane sealing the analysis region from an ambient environment; and an external micro-manipulating instrument configured to penetrate through the membrane and extract one or more components of the trapped biological sample.

In an embodiment, the present invention features a lab-on-a-chip platform. As a non-limiting example, the platform may comprise: an inlet; a plurality of inlet channels extending radially outward from the inlet; and a plurality of microfluidic devices in fluid communication with a respective one of the plurality of inlet channels.

In another embodiment, any of the microfluidic devices and methods of the present invention may comprise a filter at the inlet which prevents large material, including cells, from entering the channel. In preferred embodiments, this filter may be rinsed to clear blockages which could otherwise stop the device. In another embodiment, a flow rate of the device may be about 5 µL/min. In other embodiments, a flow rate of the device may be about 1, 2, 3, 4, 6, 7, 8, 10, 12, 14, 16, 18, or 20 µL/min.

Isolation and analysis of single migratory circulating tumor cells (CTGs) from unprocessed patient blood samples with high sensitivity holds significant promise for the understanding of blood-borne metastasis, the direct cause of ~90% cancer related deaths. The capture of these ultra-rare CTCs from the bloodstream, called liquid biopsy, reveals the molecular-level signature of a tumor with the development of high-performance CTC capture methods. CTCs can be isolated by their intrinsic biophysical characteristics such as size, stiffness, morphology, and dielectric properties. Even though diverse high-performance microfluidic separation devices have been established for CTC isolation and enrichment based on the CTC counts without labeling, e.g. inertial separation, sized-based exclusion, affinity-based capturing, acoustophoresis, dielectrophoretic sorting and deterministic chromatography the limitation of low purity of recovered CTCs remains a significant challenge because the size of CTCs may exhibit overlap with the size of leukocytes. One approach to improve the CTC selectivity, deformability-based microfluidic discrimination of CTCs has employed, resulting in higher-performance CTC capture from background cells despite their approximately identical size. In these approaches, the strong deformations may damage certain cancer cells due to the high shear stress, and the separation of cells through microstructured constrictions is limited by clogging, which reduce selectivity of cancer cells. Alternatively, CTCs can be sorted based on epithelial cell surface markers expressed predominantly on CTCs, such as epithelial cell adhesion molecule (EpCAM), however, the capture efficiency would be variable depending on the EpCAM expression level of cancer types and patients. In addition, recover of biomarker-conjugated cells from the antibody-coated surface induces cell damage and requires an additional non-trivial step for culture and enumeration. To overcome these difficulties, therefore, beyond the enumeration of CTCs, the development of identification and discrimination of CTCs without labeling in a single-cell level has prompted Significant Interest in single-cancer-cell studies.

Figure 1C:
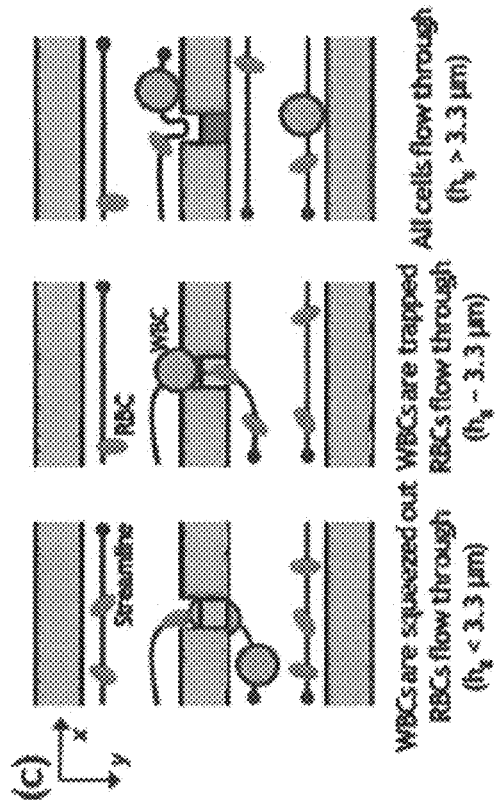
Figure 1A:
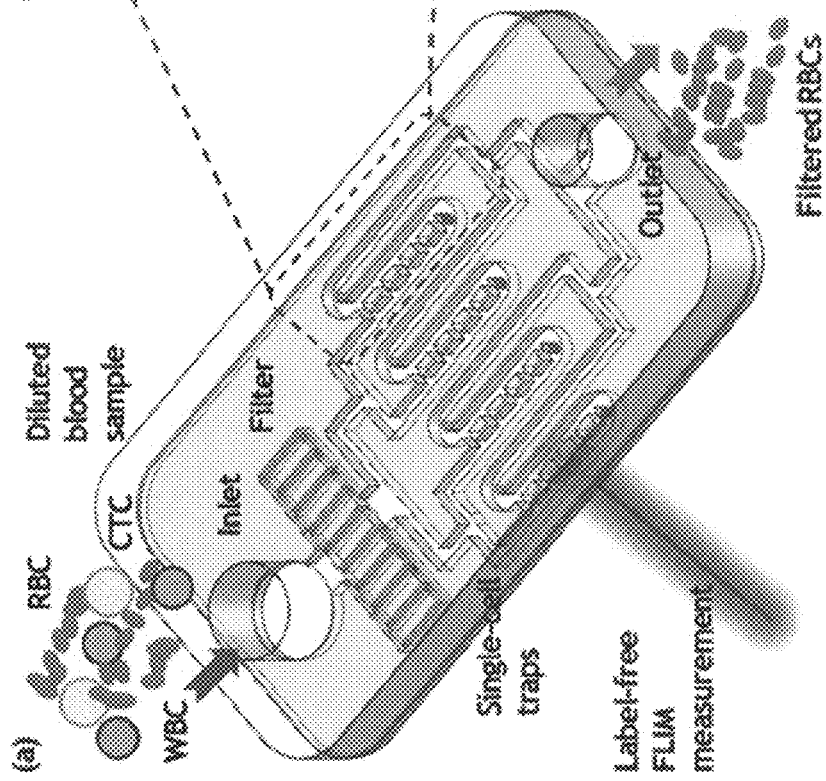
Figure 1J:
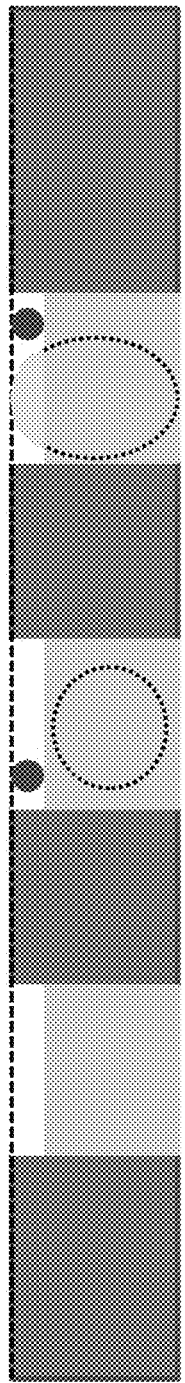
Figure 1L:
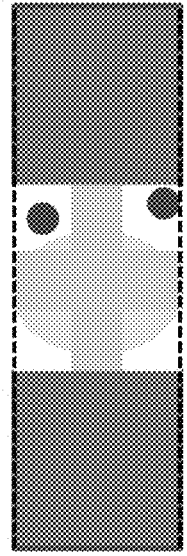
Figure 1K:
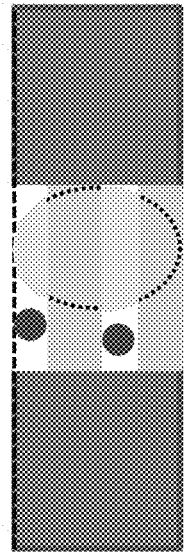

High-density and high-efficiency cell traps were utilized to separate red blood cells (RBCs) and capture WBCs and CTCs in an array formed by a serpentine channel (FIGS. 1A-1C). The device operation is based on deterministic single-cell trap which is capable of passively separation and trapping thousands of blood cells simultaneously in less than a minute with a single-cell capturing efficiency of ~80%. Although researchers have examined the possibility of single WBC and CTC Isolation from blood sample based on hydrodynamic force, current methods require a complicated microfluidic channel networks, resulting a larger device footprint and yields a low throughput. Compared to these approaches, deterministic single-cell trap allows a significantly higher efficiency of separation and capturing and easy parallelization of trapping channels to operate large sample volumes. Cells trapped in high-density microwell array are compatible with low-magnification imaging, which facilitates real-time monitoring of up to 1600 single cells by FLIM measurement in a field of view. Here the utility of deterministic single-cell trap for isolation and identification single cancer cells is demonstrated based on their average fluorescence lifetime in a label-free, gentle and scalable manner.

Results and Discussion

Microfluidic Isolation of Single White Blood Cells in the Microwell Arrays

To validate the separation and trapping principle the sorting and capturing capability of the device were tested under various operational conditions (i.e., hematocrit and input flow rate) for an Input stream of blood cell sample of patient WBC as a target cell for entrapment, RBC as a non-target cell (FIG. 2A-H). The comparison of percentage of microwell arrays that contain a single WBC ("single-cell occupancy") and >1 cell ("multi-cell occupancy") can be used to measure the performance of the trapping procedure. Also, the percentage of microwell arrays that contain a deformed single WBC due to the high shear stress was quantified. These deformed cells located at the gap area Instead of the trap, resulting the cell damage and preventing the observation of FLIM signal from the single cells, To Investigate the effect of hematocrit on WBC capture in the microwell arrays, diluted whole blood samples (0.5% to 10% hematocrit) (FIG. 2A-D) at a flow rate of 0.2 mL/h (FIG. 2E-H) were first examined. The results explained that the multi-cell occupancy became rarer with increasing hematocrit levels, while single-cell occupancy increased in proportion to the decline in hematocrit. With the increased blood concentration, more RBCs attempted to occupy the space between the traps and the loaded WBC instead of squeezing out, resulting in an increase in the multi-cell occupancy and a decrease in the sorting efficiency at higher flow rates. In contrast, decreasing hematocrit facilitates rejecting RBCs and capturing single WBCs, thereby improving the sorting efficiency and the single-cell occupancy. However, a further decrease in the hematocrit to 0.5% required longer trapping time and induced an shear stress to the already-trapped cells. Thus, 2% hematocrit was selected for implementing both the throughput and the single-cell isolation performance.

Increasing flow rate creates the cell trapping time to increase the throughput. The trapping capability of the device was tested in terms of the percentage of trapped single WBCs and multiple cells under various input flow rates from 0.2 to 1.0 ml/h. If the flow rate is increased for achieving higher throughput, the percentage of microwells that have multiple cells was decreased, however, the percentage of deformed single WBCs was dramatically increased. This means that the high flow rate causes the undesirable shear stress-induced cell deformation. The deformed cell would make a distortion of the FLIM signal due to the low cell viability. Under the input flow rate of 0.2 mL/h, the percentage of intact single WBCs was about 56.09%, higher than other flow conditions. This results in a trade-off between the trapping efficiency and throughput. If the flow rate is increased for achieving higher throughput, the pushing forces imposed on trapped single cells accelerate deformation and the cells can be released into the fluid stream from the single-cell trap without capturing. The higher number of released WBC under the high pressure also affected the WBC recovery rate.

Label-Free Identification of Single Cancer Cells Based on FLIM Measurement

Figure 3C:
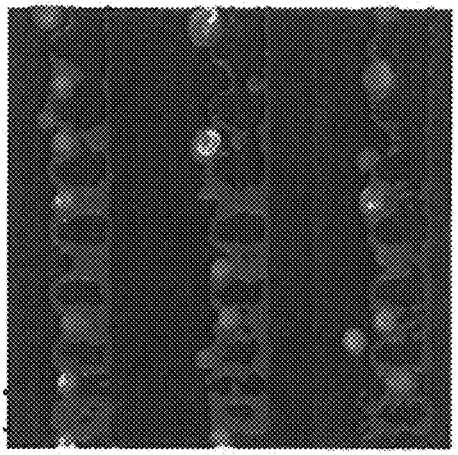
FIGS. 3A-3E illustrates identification of single cancer cells from a diluted blood sample.
Figure 3E:
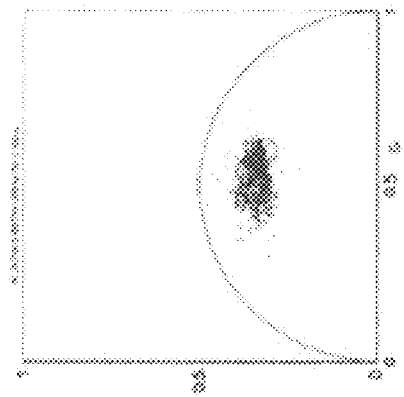
Figure 3B:
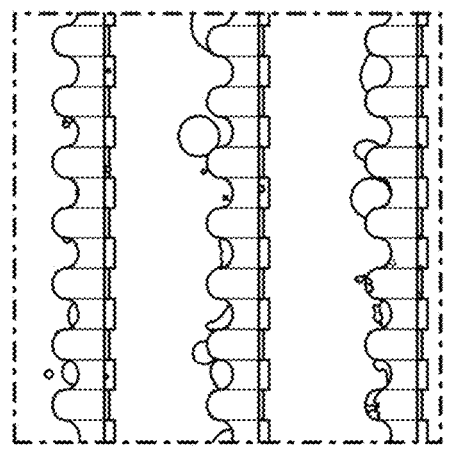
Figure 3D:
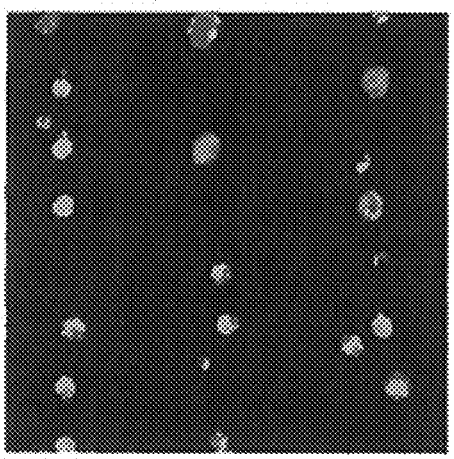
Figure 3A:
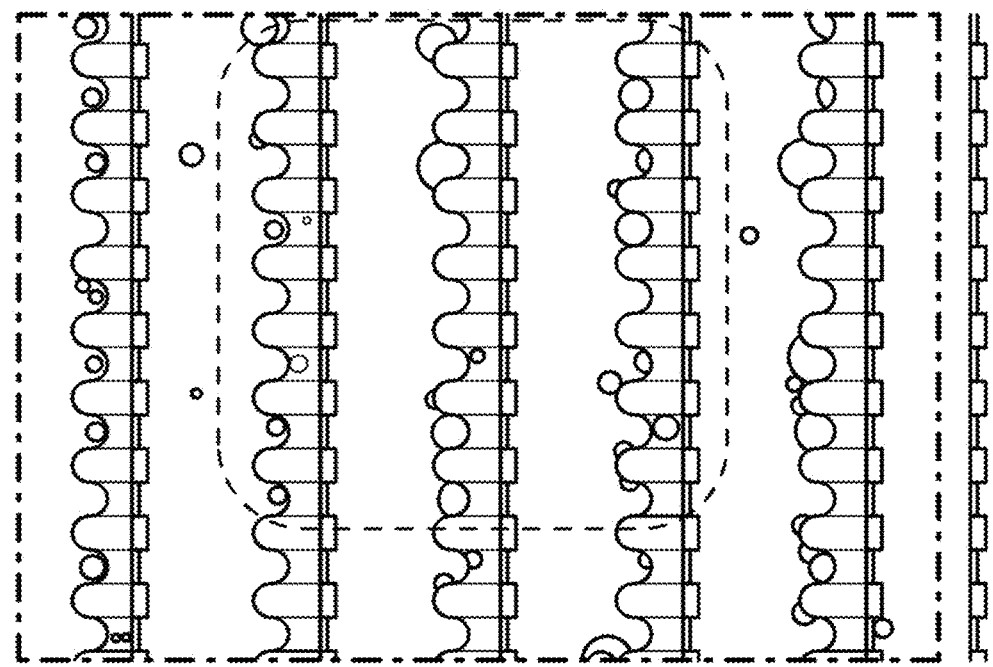

It has been shown that the combination of the phasor-FLIM Imaging and the microfluidic-trapping array allows identifying single cancer cells of different cancer types (FIG. 3A-E), After the trapping of WBCs and two different cancer cells individually MCF-7 and Hela cells—the two-photon excited autofluorescence intensity Images and the corresponding phasor plots of each cell type were acquired. FIG. 3D shows that the phasor-FLIM approach can distinguish among the WBC, MCF-7 and the Hela cells within the microfluidic devices. 2% hematocrit blood cells with a final ratio of 1:1000 cancer cells to blood cells (MCF-7 and Hela in ratio of 2:3) were injected at a total flow rate of 0.2 mL/h. This ratio results in a much greater number of cancer cells compared to that found in clinical samples, however, the ratio was chosen as a proof-of-concept purpose to show that single cancer cell separation and isolation using microwell array Is achievable. The difference in the cell phasor distributions is caused by the glycolysis contribution to total ATP production. The study found slightly higher NADH free/bound ratios in HeLa cells relative to MCF-7 breast cancer cells. This suggests that the HeLa cells are more glycolytic than the MCF-7 cells, which Is consistent with the previously reported literature. Based on these results, the ability of the parallelized microfluidic device to separate and identify heterogeneous cancer cells from a diluted human blood was examined.

Microfluidic FLIM Imaging Enables the Label-Free Discrimination of RBCs and WBCs Furthermore, RBCs also can be distinguished based on the cell phasor plot. The specific phasor-FLIM signature of the single RBCs isolated in the microfluidic trapping arrays were analyzed. (FIG. 4A-E). The super-short lifetime signature shown in the right bottom corner of the phasor plot is the hemoglobin signature (FIG. 4C). According to the literature, hemoglobin has the auto-fluorescence emission peak at 438 nm under the two-photon excitation, with extremely short lifetime. Inside the long tail in the phasor plot are signatures resulted from retinol and retinoic acid. They are essential components of serum, and involved in red blood cells' maturation, differentiation, and iron storage of hemoglobin during the oxygen carrying process. The trend in the RBC phasors suggest an indicator for diagnosing sickle cell anemia, a genetic disease due to a single mutation in hemoglobin—even at the single-cell level.

Comparative Benefits and Advantages

This method addresses a long-standing challenge in filtration of high-density RBCs and single CTC Identification from human blood sample, which produces high single-cell occupancy of WBCs and CTCs from a single input stream of cells for therapeutic use.

After the single WBC and CTC isolation, endogenous fluorescence of two different cells could be distinguished by its distinct location in the phasor plot through the FLIM measurement. The combination of phasor approach to FLIM with microfluidics provides a more quantitative and straight-forward discrimination between cancer and leukemia cells than the classic approach based on average lifetime histograms without the noise autofluorescence signal from RBCs. The Integrated microfluidic device can be made up of polymers. Compared to bulk Instruments, the microfluidic chip is cheaper, more disposable, and more suitable for mass production.

RBCs also can be distinguished within the microfluidic arrays based on the cell phasor plot. The trend in the RBC phasors suggest an indicator for diagnosing sickle cell anemia—a genetic disease due to a Single mutation in hemoglobin—even at the single-cell level.

The label-free FLM-based Identification of single cancer cells based on the deterministic single-cell trap array could represent a promising tool for detecting and quantifying cancer cells from human blood, which could also be useful for clinical applications including point of care diagnostics and cell-based therapeutics in biological laboratories.

Example 1: Fluorescence Lifetime Imaging Microscopy for the Rapid Screening and Identification of Single Leukemia Cells in Blood from the High-Density Microfluidic Trapping Array The rapid identification and analysis of single leukemia cells from blood has become critical for examination of the molecular-level tumor signatures and for early detection of human leukemia disease. However, isolation and identification of leukemia cells individually from peripheral blood requires immunological labeling and is extremely challenging due to the size overlap between leukemia cells and the more abundant white blood cells (WBCs). Herein is described a novel leukemia cell identification platform that combines deterministic single-cell separation and isolation, passive hydrodynamic trapping, and identification of single leukemia cells through phasor approach and Fluorescence Lifetime Imaging Microscopy (FLIM), which measures changes between free/bound nicotinamide adenine dinucleotide (NADH) as an indirect measurement of metabolic alteration in living cells. The single-cell array has 1,600 addressable traps, which can simultaneously filter out red blood cells (RBCs) and trap WBCs/leukemia cells. In the phasor-FLIM pixel map, trapped single leukemia cells, e.g. THP-1, Jurkat and K562 cells, exhibit significant shift towards increased free NADH as compared to WBCs, as evaluated by its own auto-fluorescence signature, indicating an increased glycolytic state for rapid proliferation. Deterministically isolated single leukemia cells in a high-density microwell array are compatible with low-magnification imaging and fast-speed fluorescence screening, which facilitates real-time monitoring of trapped single cells by FLIM measurement in a single field of view. Based on a multi-parametric analysis scheme to compare between the two spectra comprised of the phasor elements calculated from leukemia and normal WBCs, improved separation efficiency can be shown with the calculation of the area under the curve (AUC) of 1.00, which means that leukemia cell lines can be clearly differentiated from WBCs. Different leukemia cell lines could also be distinguished from each other with AUC values higher than 0.95. This system is label-free, gentle, robust and scalable, with the potential to screen blood in clinical volumes through parallelization.

The present invention features a metabolic-based, label-free leukemia cell identification method that combines (i) passive hydrodynamic control for separation and trapping single living leukemia cells simultaneously in a continuous flow with, (ii) rapid screening of single-leukemia cells from normal WBCs via phasor-FLIM imaging of the single cells' autofluorescence signatures. (FIG. 5A) Blood sample processing is easy to operate via the microfluidic trapping array with 1,600 traps filled within 3 mins. In the phasor-FLIM, each endogenous fluorescence can be distinguished by its distinct location in the phasor plot. Each cell has its own signature on the phasor plot, corresponding to its metabolic patterns and the relative concentration of autofluorescent metabolites. It may be that the quantification of free NADH microfluidically presents an opportunity to functionally distinguish metabolically active leukemia cells from other nontumor cells such as WBC in blood. With the combination of a single-cell microfluidic device and the phasor-FLIM, this rapid screening platform enables high-throughput screening of NADH from a large number of cells at single-cell resolution, leading to detection of metabolically active leukemia cells compared to the WBCs. Instead of the traditional phasor analysis, the present invention uses a multiparametric analysis scheme to compare between the two spectra comprised of the phasor elements calculated from leukemia and normal WBCs for quantitative separation and statistical calculation. The presented platform may be the first to enable high-density single-cell trapping simultaneously with RBC filtering and to achieve rapid label-free screening of single leukemia cells through non-invasive metabolic imaging.

Material and Methods
Fabrication of the Microfluidic Device

A microfluidic device was fabricated in PDMS by the soft lithography method and consisted of a pre-filter region and a deterministic single-cell trapping region. SU-8 structures were patterned on a silicon wafer via standard multi-step photolithography. Liquid PDMS mixed with a curing agent (ratio of 10:1) was cast on the mold and cured for 3 h in a convection oven at 65° C. for complete cross-linking. Then the PDMS microchannel was then irreversibly bonded to a flat glass slide after treatment with oxygen plasma for 60 s. There were pillar structures in the inlet channels with a pitch of 25 µm that function as pre-filters to prevent the introduction of cancer cell aggregates into the trapping region. There was an outlet channel for the separated RBCs. The present invention features 16 parallel trapping channels for the purpose of increasing the throughput of cell separation and isolation. The height and the width of the main channel were 18 and 40 µm, respectively, Width and length of the traps were 10 and 15 µm, respectively.

Cell Culture

THP-1 (human acute monocytic leukemia cell line), Jurkat (human acute T cell leukemia cell line), and K562 (human chronic myelogenous leukemia cell line) cells were cultured in RPMI1640 medium supplemented with 10% fetal bovine serum. In particular, for THP-1 cells, 0.05 mM 2-mercaptoethanol was added as a metabolic supplement. Cells were passaged every 2-3 days following standard protocols and cultured in a humidified incubator at 37° C. with 5% CO2. The human blood sample was collected from UCI General Clinical Research Center with Institutional Review Board (IRB) approval.

Instrument Set-Up for Imaging

Fluorescence lifetime images of the WBC/leukemia single-cell arrays were acquired utilizing a Zeiss® 710 microscope coupled with a Ti: Sapphire laser system and an ISS A320 FastFLIM unit. SimFCS software, was used to control the system for FLIM data acquisition. The single-cell array was placed in the 37° C., 5% CO2 environment during the imaging to secure the cell viability, and was excited via two-photon excitation at a wavelength of 740 nm with a laser power of 5 mW. A 40×1.2 NA oil-immersion objective was used, and a dichroic filter (690 nm) separated the auto-fluorescence signal from the laser light. For FLIM image acquisition, fluorescence was detected by a photo-multiplier using a bandpass filter of 460/40 nm, which covers the emission wavelength of free and protein-bound NADH. Images in the size of 256×256 pixels were acquired at the scan speed of 25.21 µs per pixel, and the scanning was continued until 100 counts in the brightest pixel of the images were collected. FLIM calibration of the system was performed by measuring the known lifetime of Coumarin 6 dissolved in ethanol with a single exponential decay of 2.5 ns. Typically, the acquisition time of one selected region of interest in the single cell array, which can include as many as 100 single cells, was less than 1 min.

Theory of Phasor-FLIM Approach

The acquired FLIM data of the single-cell array was analyzed in a phasor approach using SimFCS software. Briefly, each pixel of the FLIM image was transformed into one pixel in the phasor plot through Fourier transformation, in which the sine component of the fluorescence intensity decay curve of that pixel was transformed into its s axis coordinate, and the cosine component was transformed to is g axis coordinate in the phasor plot. The detailed theory and transformation process were explained in the previous study. On the phasor plot, a cursor may be used to highlight a cluster of points that corresponded to the pixels in the FLIM image with a particular lifetime range.

Results

Design and Operating Principle of the Platform

Figure 10:
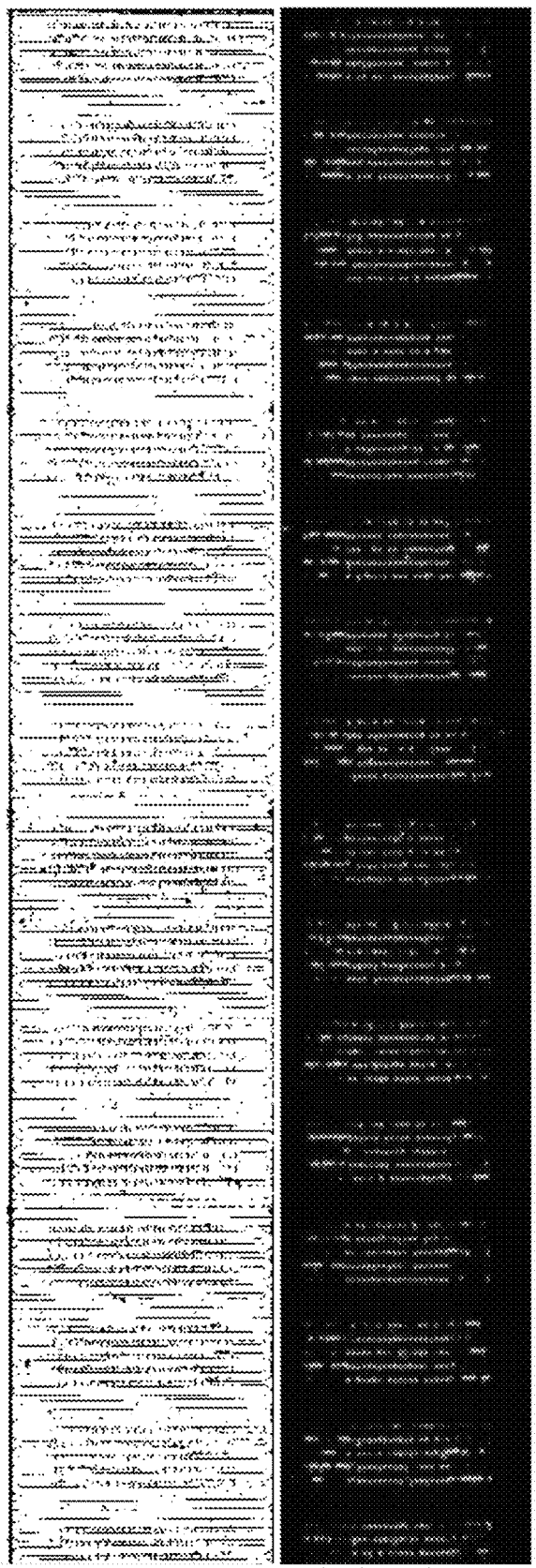
FIG. 10 shows a high-throughput microfluidic trapping array containing 16 identical arrays of highly packed 100 single-cell traps, designed with small dimensions to fit within a microscopic field of view and which can be filled within 3 mins, enabling the observation and identification of every single leukemia cell flowing through the channel.

The presented high-density single-cell array consists of a serpentine-shape microfluidic channel with size-selective traps arrayed along each row, by which single WBCs and leukemia cells are captured passively and deterministically with RBCs filtered out simultaneously because of smaller in size (FIG. 5S). At the pre-filter with 25 µm pitch and 18 µm height, the unwanted cell aggregates were successfully blocked, and single leukemia cells, WBCs, and RBCs passed smoothly and flew into the single-cell trapping region. The cell aggregates would cause the microchannel clogging at the single-cell trapping region and decrease the single-cell occupancy. Under the flow rate of 0.2 mL/h, only 4.74% of leukemia cell aggregates were flown through the pre-filter. The device operation is based on a deterministic single-cell trap capable of passively separating and trapping millions of blood cells simultaneously in less than a minute with a single-cell capturing efficiency of 80%. Each trapping unit has a smaller height of the trap than the height of the main delivery channel, resulting in a gap area (hg). The gap area makes the perpendicular flow to deform and migrate RBCs, while WBCs and leukemia cells can be pushed into traps, and the combination of perpendicular deformation and horizontal delivery flow enables the continuous blood cell filtration process. The height of hg is of critical in determining the WBC/leukemia capturing efficiency, as larger hg leads to WBCs/leukemia cells squeezing during RBC filtration, and smaller hg would prohibit both RBC passing through and WBC/leukemia trapping (FIG. 5C). The proposed high-throughput microfluidic trapping array contains 16 identical arrays of highly packed 100 single-cell traps, designed with small dimensions to fit within a microscopic field of view and can be filled within 3 mins, enabling the observation and identification of every single leukemia cell flowing through the channel (See FIG. 10).

Figure 6A:
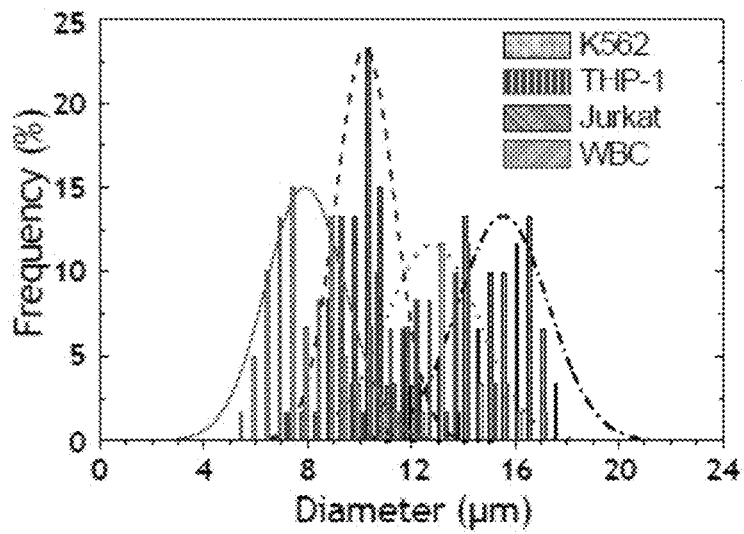
FIGS. 6A-6F show cell size characterization and single-cell trapping efficiency optimization
Figure 6B:
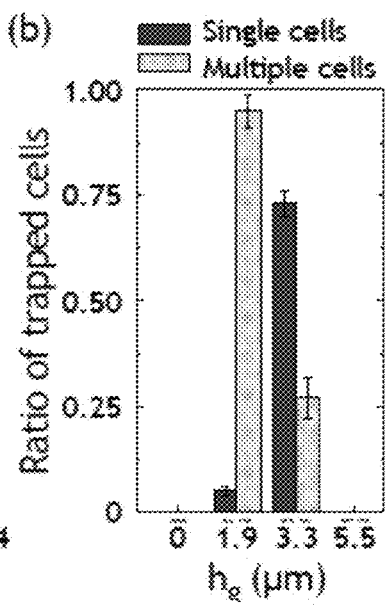
Figure 6C:
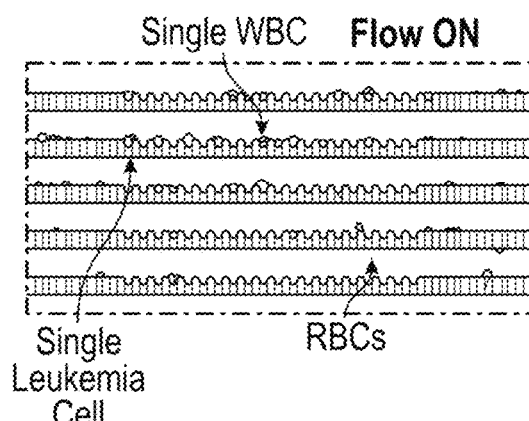
Figure 6D:
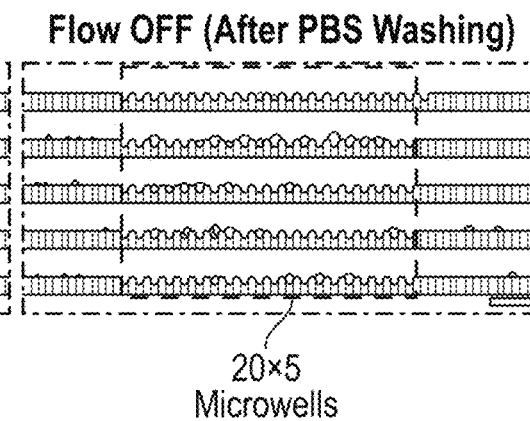
Figure 6E:
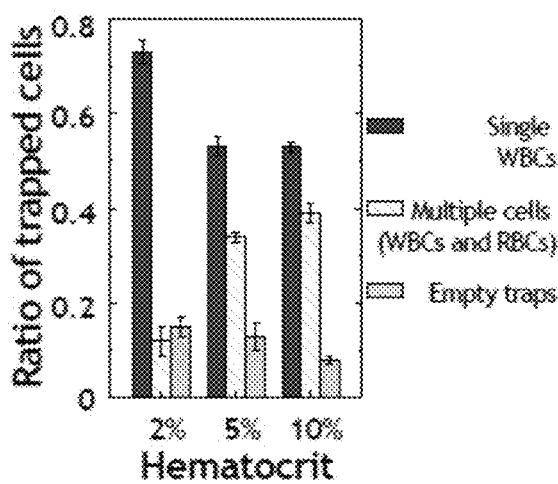
Figure 6F:
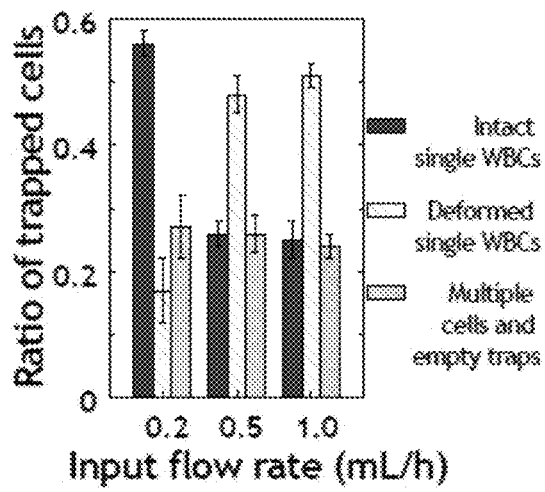

Most of the normal WBCs and leukemia cells have a diameter ranging from 8 to 20 µm, and there exist significant size overlap based on the measurement of normal human WBCs, and three different types of leukemia cells: THP-1, Jurkat, and K562 (FIG. 6A). But both normal WBCs and leukemia cells are larger than RBCs, which have a disk shape with a diameter of ~6.2-8.2 µm and a thickness at the thickest point of 2-2.5 µm. Therefore, while leukemia cells cannot be separated from WBCs purely by size, RBCs can be successfully filtered out within the microfluidic trapping arrays. It may be that RBCs are not constrained by the gap area constrictions because of their extreme deformability and large surface area compared to WBCs and leukemia cells. The percentage of single-cell occupied traps was tested according to different hg of 0, 1.9, 3.3 and 5.5 µm, respectively (FIG. 6B). If hg is 0, no cell trapping was observed within the microwell arrays. It was found that the single-cell trapping efficiency was about 73.48% with hg of 3.3 µm, while no cell was observed at the trap with hg of 1.9 and 5.5 µm. Especially, when the hg was much lower than the RBC diameter (hg 1.9 µm), RBCs were stuck at the trap and could not migrate through the gap area, resulting in increased number of multiple-cell trapping. In contrary, when the hg was much higher than the RBC diameter and similar to the WBC diameter (hg 5.5 µm), all blood cells including WBCs and RBCs were passed through the gap area instead of being trapped in the single microwells. The results demonstrate that the appropriate hg is able to filtrate only RBCs and isolate deterministically single WBCs as well as cells that have a larger diameter than WBCs such as leukemia cells. An optimal hg ~3.3 µm was chosen to operate a device for WBC isolation applications. FIG. 6C shows that the bright-field microscopic image of trapping WBCs and leukemia cells (K562) within the microwell arrays with hg=3.3 µm. After turning off the sample flow and introduction of PBS, all RBCs were removed toward the outlet and only WBCs and leukemia cells were remained at the microwell arrays. Deterministic single-cell isolation of blood under various rheological conditions was explored, demonstrating highly efficient trapping of single leukemia cells and white blood cells in a high-density microwell array (FIGS. 6E and 6F, FIG. 11A-F). 2% hematocrit blood was introduced at under 0.2 mL/h for implementing both the throughput and the single-cell isolation performance.

Phasor-FLIM Measurement of WBC and Leukemia Single-Cell Arrays

Single cells of 4 different populations, WBC (FIG. 7A), THP-1 (FIG. 7B), Jurkat (FIG. 7C), and K562 (FIG. 7D), were trapped in separate microfluidic arrays under the input flow rate of 0.2 mL/h, respectively, and are excited via two-photon excitation at 740 nm. The transmission images of the single-cell arrays, the magnified images of the selected regions of interest (ROI), and the NADH autofluorescence intensity images of the ROI are shown in FIG. 7A-D from the panel (i) to (iii). Phasor transformation was then applied to the acquired FLIM data and plotted the phasor-FLIM pixel plots of the single-cell arrays as shown in FIG. 7A-D panel (iv). he fluorescence intensity decay at each pixel of the FLIM image was transformed into a single point in the phasor plot (as defined in the Materials and Methods section), in which the s and g coordinates for every pixel of the image, Fourier sine versus the Fourier cosine components of the fluorescence decay curve, were plotted on the y and x-axis where the x coordinate spans from 0 to 1 and the y spans from 0 to 0.5. Based on the pure chemical phasor fingerprints, signatures of the WBC/leukemia single-cell arrays are mainly generated from the combination of intrinsic autofluorescence biomarkers, free and enzyme-bound forms of NADH, which have a fluorescence lifetime shift from ~0.4 ns at free stage to 3.2-3.4 ns at bound stage. To further visualize the difference of the phasor-FLIM signatures between different the cell populations and the cellular heterogeneity within the same population, the average s and g values of individual cells of WBC (square), Jurkat (circle), THP-1 (triangle) and K562 (diamond) were plotted in the scatter diagram of FIG. 7E and the distribution of cell phasors of the WBCs are significantly different from the group of leukemia cells. A comparison of data pairs demonstrated statistically significant differences in cell phasors for each cell types (p=3.60×10-53, Student's t-test, *p<0.05). Leukemia cells are shifted toward the lower right direction in the phasor plot compared to WBCs, demonstrating a shorter lifetime, and therefore indicating a higher ratio of free to bound NADH. This can be explained by the Warburg Effect, in which rapid-proliferating tumor-like cells, i.e. leukemia cells, have stronger glycolysis in glucose metabolism to support fast ATP consumption and have a higher ratio of free/bound NADH; while differentiated cells, like WBCs, have stronger oxidative-phosphorylation (OXPHOS) and have a higher bound/free NADH ratio. The phasors of the three leukemia cell lines also show inner-population heterogeneity in the scattered plot.

Differentiating Different Leukemia Cell Lines Via Multi-parametric Analysis of Phasor-FLIM While the single-cells' phasor values of 3 types of leukemia cell lines (THP-1, Jurkat, and K562) were located closely in the scatter plot, they can still be quantitatively differentiated by a multiparametric analysis scheme that splits the phasor points in 4 equidistance segments based on the height of peak of the phasor distribution and calculates the average phasor coordinates (g and s) in each segment. A spectrum of 8 parameters specific to the phasor distribution of each sample is created based on the above, and quantitative separation can be applied to the spectra of two different groups, the control (C) and the test (T). The average spectrum of each group and the deviation of each member from the average can be calculated, and if the spectrum of an unknown sample is equal to the average of C then the separation index SI=−10, if it is equal to the average of T then SI=+10, and if the spectrum is at equal distance from C and T then SI=024. An SI histogram can be plotted based on the number of counts at each SI value, and the area-under-the-curve (AUC) value of this comparison can also be calculated.

As is shown in FIG. 8A, WBCs are the C group, and all 3 types of leukemia cells are the T group. While the SI of T group is broadly distributed, indicating the heterogeneity of the leukemia cell population, there is no overlapping with the SI distribution of WBCs, and the AUC=1.000, which means that leukemia cell lines can be clearly differentiated from WBCs based on the multiparameter scheme, confirming the scatter plot in FIG. 7E. Three training sets that separate each 2 of the 3 leukemia cell lines are also established using multiparameter analysis of the cell-line specific phasor distributions, and the SI histograms are plotted (FIG. 8B). The AUC values of each two comparisons are all higher than 0.950 (AUCTHP-1-Jurkat=0.957, AUCK562-THP-1=0.981, and AUCK562-Jurkat=0.987), suggesting a statistically powerful separation between each of the two leukemia cell lines. Importantly, this classification is performed at a single-cell level rather than as a population metric and across three samples.

Figure 9A:
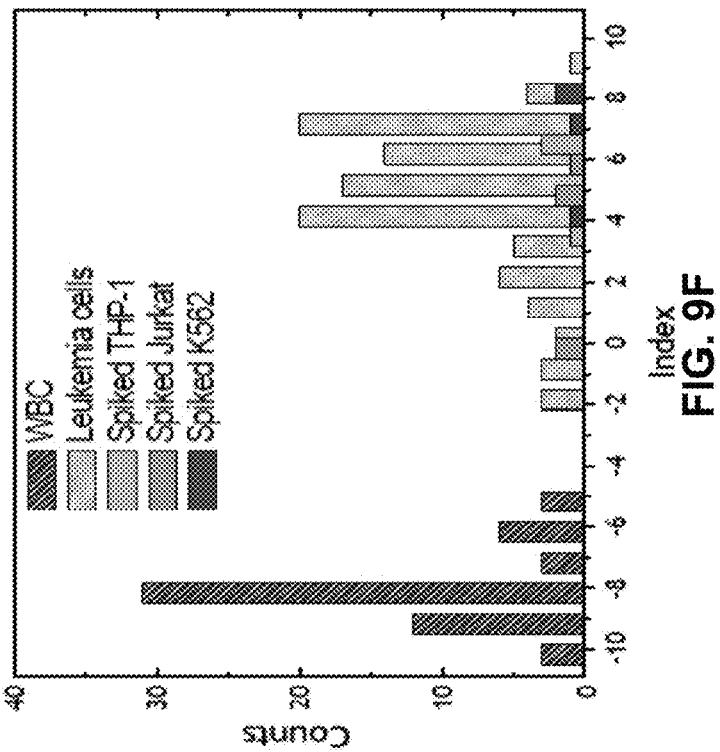
FIGS. 9A-9F show the screening of leukemia cells from normal WBCs in the leukemia cell-spiked blood samples via phasor-FLIM imaging of the single-cell trapping array. Scale bars: 50 µm.
Figure 9B:
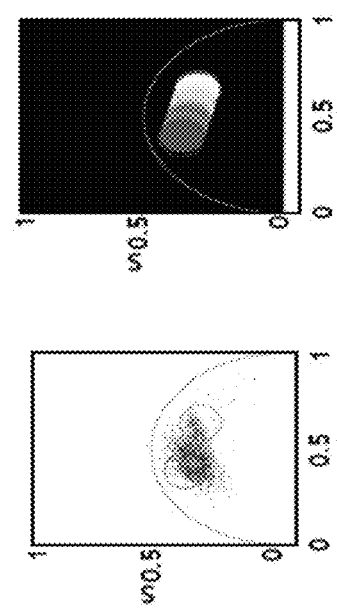
Figure 9C:
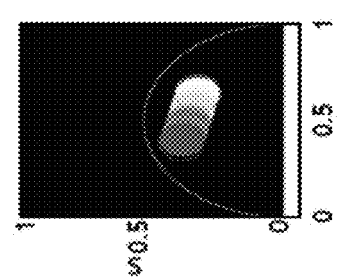
Figure 9D:
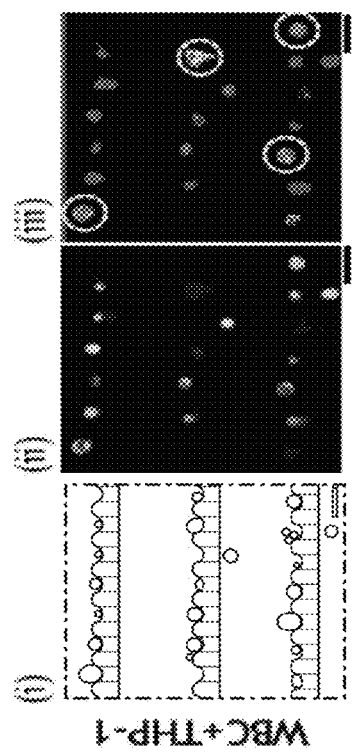
Figure 9E:
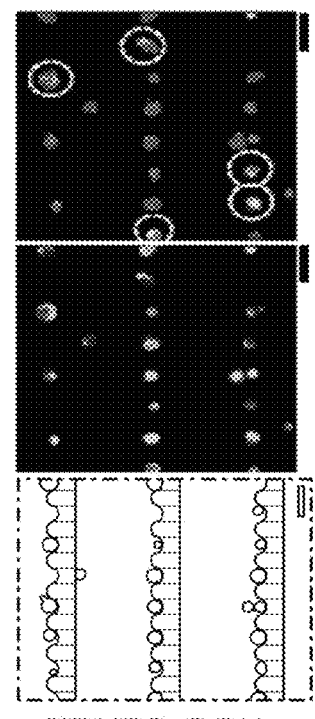
Figure 9F:
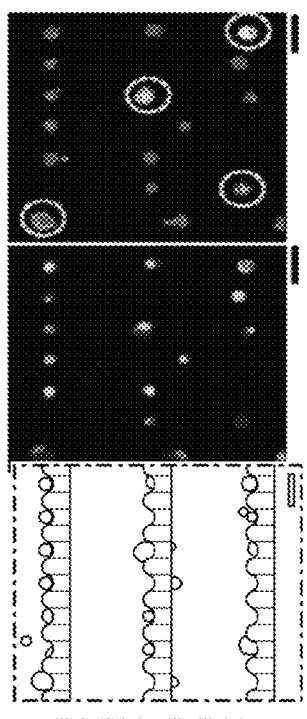

Rapid Single Leukemia Cell Screening from Leukemia-Cell-Spiked Blood Samples Via Phasor-FLIM Imaging of the High-Density Trapping Array After identification of the difference in the phasor-FLIM fingerprints of single WBCs and leukemia cell lines (THP-1, Jurkat, and K562), rapid label-free single leukemia cell screening was conducted in leukemia-cell-spiked human blood samples. THP-1, Jurkat, and K562 cells were spiked into human blood at a 1 to 5 ratio to WBCs, separately, in order to mimic the blood sample of patients with different types of leukemia, and the diluted whole blood samples (2% hematocrit) were introduced into the high-density single-cell arrays under the flow rate of 0.3 mL/h (FIG. 9A-C(i)). Then the single-cell arrays' NADH autofluorescence emission (FIG. 9A-C(ii)) and fluorescence lifetime data was collected at 740 nm, two-photon excitation and plotted the lifetime maps (FIG. 9A-C(iii)) by linking the higher bound/free-NADH-ratio group and the higher free/bound-NADH-ratio group in the total phasor distribution plot of all the trapped single cells (FIG. 9d). Different types of the spiked single leukemia cells were obviously distinguished from normal WBCs as highlighted in the white-dashed circles in the lifetime maps (FIG. 9A-C (iii)), as the spiked leukemia cells have more components in the white and blue color, while normal WBCs consist of more red and pink color components. The significant shift toward a higher free/bound NADH ratio and shorter lifetime region of leukemia cells compared to WBCs is because the leukemia cells are in a rapid proliferating stage and utilize more glycolysis to facilitate rapid generation of ATP, while WBCs use OXPHOS as the major metabolic mechanism to digest glucose more completely but generate ATP slower. Another non-negligible results shown in the lifetime map is the cell-to-cell heterogeneity among the same population, which represents the unique metabolic pattern of specific cells, and can be further analyzed to separate sub-populations of interest. For instance, subgroups of WBCs, e.g. neutrophils, eosinophils, basophils, lymphocytes, and monocytes, might be able to be differentiated based on their autofluorescence patterns via single-cell phasor-FLIM, Apart from color-coding based screening from the lifetime maps, a more quantitative screening of single-leukemia cells can be achieved by loading the phasor-FLIM information to the multiparametric separation training sets that were established in FIG. 8A. As is shown in the SI histogram in FIG. 9F, in which the phasor-FLIM signatures of the single cells (dotted white circle) were compared with WBCs (C group) and the combined population of 3 leukemia cell lines (T group), and all the circled cells were calculated to have positive SI index values, confirming their identity as leukemia cells. Also, different types of spiked leukemia cells have different SI values, and the type of a potential known leukemia cell can be further identified by loading its information to the leukemia cell type comparison training sets (FIG. 8B). As the FLIM data collection of each laser scanning area containing 100 single-cell traps takes less than 1 min, the leukemia cell screening of the total 1,600 traps could be achieved within 16 mins.

Discussion

Here it has been shown that the microfluidic single-cell phasor FLIM can map a metabolic fingerprint of single leukemia cell without any labels and can differentiate normal and tumor leukocytes with a similar size according to their metabolic state. A significant difference is seen between the WBC group and leukemia cell group based on a multiparametric analysis scheme within the microfluidic device.

It has been found that the high-density and high-efficiency cell traps can be utilized as a microfluidic separator of leukocytes and leukemia cells from the diluted blood sample. Because RBC has a smaller diameter than hg and an extremely high deformability, the gap area allows the escape of RBCs from the high-density cell traps, while larger leukocytes and leukemia cells could be isolated sequentially and individually. The scalable design of high-density single-cell traps speeds up the process of metabolically characterizing thousands of cells to detect leukemia in a short amount of time.

Microfluidic single-cell phasor FLIM is particularly relevant to the separation of tumor cells from blood where tumor cells may not be easily discriminated from leukocytes based on size alone. Especially, because the diameter of leukemia cells have significant size overlap with leukocytes, recent high-performance microfluidic separation devices suffered from a limited number of isolated leukemia cells. Also, the metabolic differences in terms of the free/bound NADH ratio between two groups are discernable. It has been shown that microfluidic single-cell phasor FLIM with multiparameter analysis can perform the quantitative discrimination between normal WBCs and leukemia cells without the noise autofluorescence signal from RBCs. This is the first demonstration to discriminate single leukemia cells from WBCs using phasor-FLIM based on the difference of free/bound NADH ratio between two groups.

Figure 12:
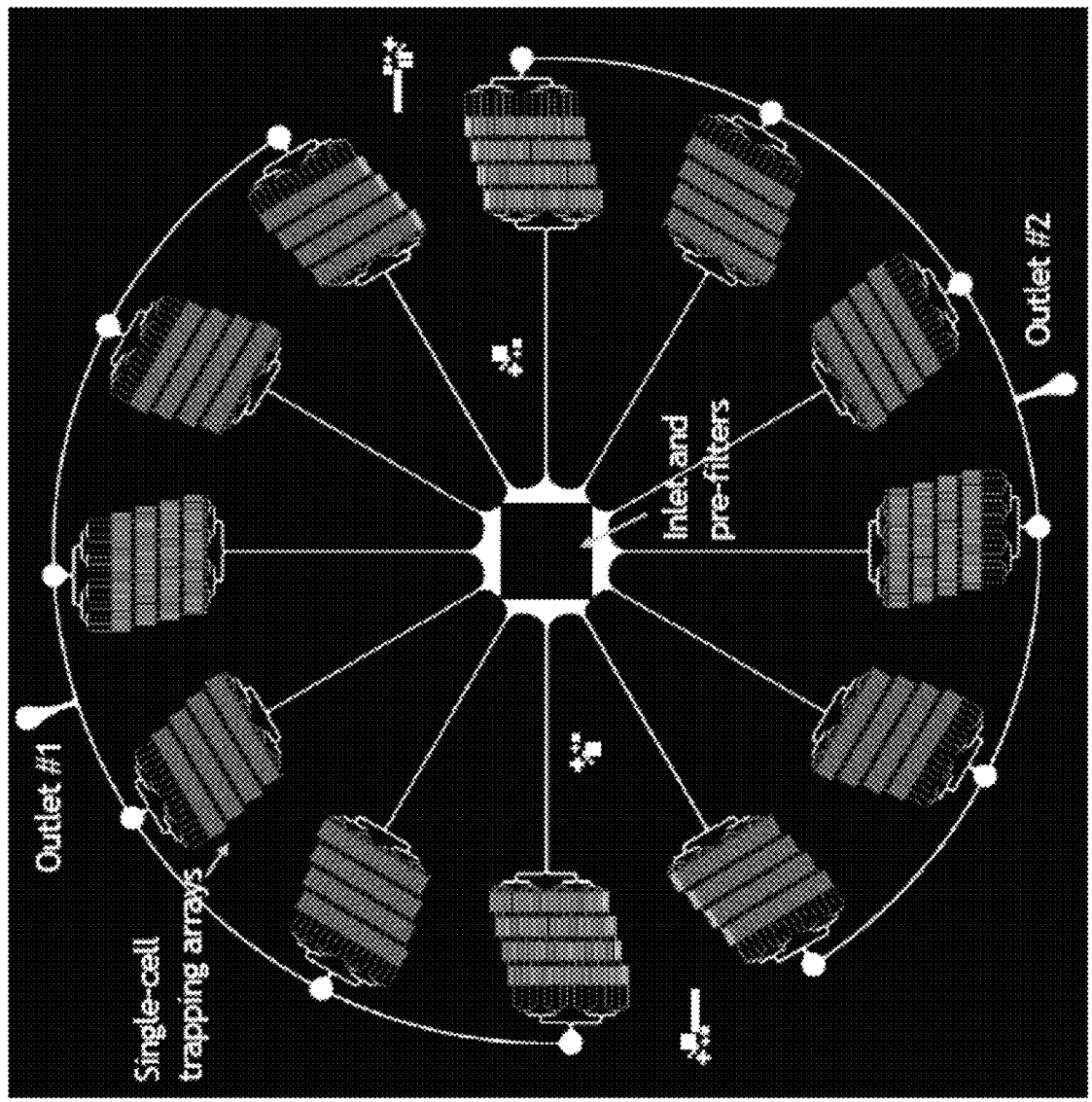
FIG. 12 shows a photograph of a device arrayed with 12 radially arranged channels integrated into a PDMS device.

To expedite leukemia detection and improve targeted treatments, it is crucial to quickly screen the abnormal leukocytes that might allow determination of effective treatment to be made in real time at the bedside. The proposed microfluidic isolation platform based on their metabolic properties of cells has advantages over a conventional flow cytometry. Fluorescence-activated cell sorting (FACS) is a representative approach in flow cytometry to categorize heterogeneous samples in a high-throughput manner. But it requires a time and effort consuming process to fluorescently tag cells with expensive antibodies that could potentially lead to irreversible cell damage and change in intrinsic cell properties. Moreover, FACS cannot easily detect the single-cell heterogeneity and is not sufficiently applicable to single-cell transcriptomic analysis that unveils comprehensive information of leukemia cell behavior and their heterogeneity according to expressions of marker-genes. Also, clinical deployment of single-cell FLIM for leukemia monitoring, however, would require sampling within minutes. One of the main challenges in the presented platform can process 2% diluted blood. The device can take care of a higher hematocrit level sample and be massively parallelized to move towards higher throughput. It was determined that the proposed device could be arrayed with 12 radially arranged channels integrated into the 3-inch PDMS device that can deal with large volumes of blood samples (FIG. 12). It was simply calculated that when 2% diluted blood is tested at 0.2 mL/h, 76,800 single leukemia cells and WBCs can be isolated in 2 min. The high-density single-cell trapping array can be integrated as a multi-step-integration feature with various kinds of microfluidic cell separator. For example, the microfluidic erythrocytes removal modules such as inertial microfluidics, acoustics, and microfilter arrays can be easily combined as an upstream pre-sort sample preparation. This capability is notably crucial when phenotyping of the patient-derived circulating leukemia cells from whole blood is required.

Peripheral WBCs consist of several subpopulations such as lymphocytes, monocytes, neutrophils, eosinophils, and basophils. Phenotypic and functional analysis of single peripheral WBCs present valuable clinical information based on their numbers, compositions, and functional responses, for example, (i) the production of interferon gamma (IFN-γ) by T-cells which correlates with the immune response against tuberculosis infection, (ii) the increased neutrophil count caused by bacterial infections often cause an increased neutrophil count, while the increased number of lymphocytes due to the viral infections and auto-immune disorders, and (iii) the peripheral blood lymphoblast percentage is an important index for diagnosis and prognosis of acute lymphoblastic leukemia (ALL). Thus, the differential counting of WBCs from smaller quantities of blood is crucial for point-of-care diagnosis. Label-free isolation and non-invasive differential discrimination of single leukocytes via phasor-FLIM33 will facilitate in vitro analysis of immune responses where preservation of immune cell phenotypes and alter the conventional WBC counting and phenotyping.

The existence of a highly tumorigenic subpopulation of cancer cells, especially cancer stem cells (CSCs) in heterogeneous tumor mass plays a role in tumor development, metastasis and construction of the entire spectrum of bulk tumor cells. The current platform based single-cell FLIM identification would be applicable to screen single CSCs according to differential drug responses in the entire tumor population and would enable exploration of tumor heterogeneity and differential response to drugs. After the phenotyping, the single cells of interest can be cultured within the microfluidic device, further analyzed in situ and retrieved upon adapting various techniques such as optical DEP, pipetting, and laser-based manipulation. Cellular information from isolated single living leukemia cells can be extracted and/or inserted via selective intracellular probing using dielectrophoretic nanotweezer (DENT) after the phasor-FLIM analysis. This can enable functional characterization of the protein encoded by the introduced DNA to help elucidate how leukemia cells function.

CONCLUSIONS

In summary, deterministic single-cell trap array represents a novel method of size-based cell separation, enabling effective single-cell capture, easy measurements of time-integrated fluorescence intensity through phasor-FLIM, and quantitative and straightforward discrimination between normal WBC and leukemia cells without the noise autofluorescence signal from RBCs. The single cell trapping array was redesigned with the gap height (hg) of 3.3 µm to enable the filtering of RBCs and the capturing of 1,600 single WBCs and leukemia cells simultaneously from 2% hematocrit blood. After the single-cell isolation within the microwell array, the phasor-FLIM pixel map of trapped single leukemia cells and WBCs was evaluated by its own auto-fluorescence signature and differentiated based on the significant shift towards increased free NADH. The AUC value obtained between the single WBC group and the single leukemia cell group from the comparison of four parameters using the multiparametric method is 1.000, demonstrating the perfect separation between two groups via single-cell phasor-FLIM. The label-free FLIM-based identification of single leukemia cells based on the deterministic single-cell trap array could represent a promising tool for detecting and quantifying leukemia cells from human blood, which could also be useful for clinical applications including point-of-care diagnostics and cell-based therapeutics in biological laboratories.

Example 2: A Non-Invasive Single-Cell Transcriptomic and Metabolic Analysis Microfluidic Array Single-cell analysis provides comprehensive information and reveals intracellular heterogeneity of the cell population, which is of critical importance in medical and biological research. However, most of the developed single-cell biomolecular and biochemical assays require cell lysing and complicated purification/labeling processes. Here is presented an integrated platform capable of collecting single-cell transcriptomic and metabolic information in a non-invasive and label-free manner. Cells are trapped in a 1-µm-thick PDMS membrane-sealed single-cell array, and a modified AFM probe penetrates through the membrane to extract single-cell mRNAs by dielectrophoresis (DEP), coupled with fluorescence lifetime imaging microscopy (FLIM) to acquire metabolic patterns through single-cells' intrinsic autofluorescence.
Materials and Methods The cell-trapping array, which was made by soft lithography casting of the SU-8 mold, consisted of a serpentine channel with 20 grooves arrayed along each row (FIG. 1A), and was sealed by oxygenplasm bonding to a 1-µm-thick PDMS membrane fabricated by spin-coating PDMS-hexane mixture (1:2) at 5000 rpm, 5 min. The modified AFM probe was a highly doped silicon probe coated with a 20 nm $SiO_2$ insulation layer and a 10 nm/30 nm Cr/Au outer electrode, with its end cut so that the Si core (inner electrode) was exposed. When an AC field was applied between the inner and outer electrodes, a DEP force ($FDEP=[(V\alpha)/2]\Delta|E|^2$, V, cell volume; α, polarizability) strong enough to attract mRNAs to the tip-end was produced (FIG. 1B). The extracted mRNAs underwent RT-qPCR to reveal the expression levels of target genes. The single-cell array was then excited by two-photon excitation at a wavelength of 740 nm, and the autofluorescence emission was collected in the range of 430-550 nm, covering the emission wavelengths of free and bond forms of nicotinamide adenine dinucleotide (NADH). NADH is the main metabolic coenzyme involved in oxidative phosphorylation and glycolysis, and the free-to-bond NADH ratio reports metabolic changes associated with carcinogenesis and differentiation. Since free and bond forms of NADH have distinct autofluorescence intensity decay time (i.e., fluorescence lifetime), cells with different metabolic patterns have different free-to-bond NADH ratios, and therefore, locate at different positions in the phasor-FLIM plot.
Results and Discussion Every 100 cells were trapped in 20 s with a single-cell occupying efficiency of 94±4% (FIG. 13A). When MCF7 breast cancer cells and U937 monocytes (a type of white blood cells) were trapped together in the single-cell array, although they were of similar size and could not be distinguished by morphology, the gene-expression fingerprint of EPCAM, HER2, and CD45 generated from the probed-out mRNAs clearly told the cell identity (FIG. 13C). Coupled with FLIM, benign tumor cells could be identified from malignant tumor cells. For example, MCF7 cells (benign tumor cell line) were located in the upper-left position of HeLa cells (malignant tumor cell line) in the phasor-FLIM plot (FIG. 13D-E). This was due to the reason that malignant tumor cells have stronger glycolysis than oxidative phosphorylation, there for having a higher free-to-bond NADH ratio, shifting toward the right-bottom position in the phasor-FLIM plot. According to literature, the glycolysis contribution to total ATP production is ~21% and 9% in HeLa and MCF7 cells, respectively.

Example 3: Isolation and Identification of Single Plant Cells

Unique and Novel Features

The high-density and high-efficiency cell traps were used to separate plant cells and debris in an array formed by a serpentine channel. This demonstrates the utility of deterministic single-cell trap for isolation and identification of single plant cells based on their average fluorescence lifetime in a label-free, gentle and scalable manner. The microfluidic single-cell trapping array consists of a serpentine channel with 20 traps along each row. The channel height is 120 µm, and the trap size is 75 µm, which is similar to the diameter of the microspores. For each single-cell trap, there is a 10 µm-height gap area to enable the perpendicular flow to push the cell into the trap. Gunk debris is blocked by the pillar array at the inlet, and small debris passes through the gap area and is filtered out.
Results and Discussion
Microfluidic Isolation of Single Plant Cells:

The combination of the phasor-FLIM imaging and the microfluidic-trapping array allows identifying single plant cells (FIGS. 14A-14F). In this experiment, tetrad cells (FIG. 14A) and separated single cells (FIG. 14C) from Johnston, as well as late uninucleate microspores (FIG. 14E) were trapped in the single-cell trapping array and imaged at 740 nm two-photon excitation. The autofluorescence emission in the range of 420 nm 500 nm was collected, and their corresponding fluorescence lifetime was calculated and plotted in the phasor plots (FIG. 14B, FIG. 14D, FIG. 14F). When comparing the phasor plots, there was no significant difference between tetrad cells and separated cells. This is reasonable as the single cells may just escape from the tetrad capsules and have not undergone significant metabolic changes. On the other hand, late uninucleate microspores showed obvious different lifetime patterns compared to tetrad cells/separated single cells. Microspores have unique lifetime signatures at the bottom-right corner of the phasor plot, which may be due to microspores being more developmentally mature and having well-defined cell walls compared with tetrads and just separated single cells. In addition, the average lifetime of microspores shifted towards shorter lifetime side compared to tetrad/single cells.

Figures 15A, 15B:
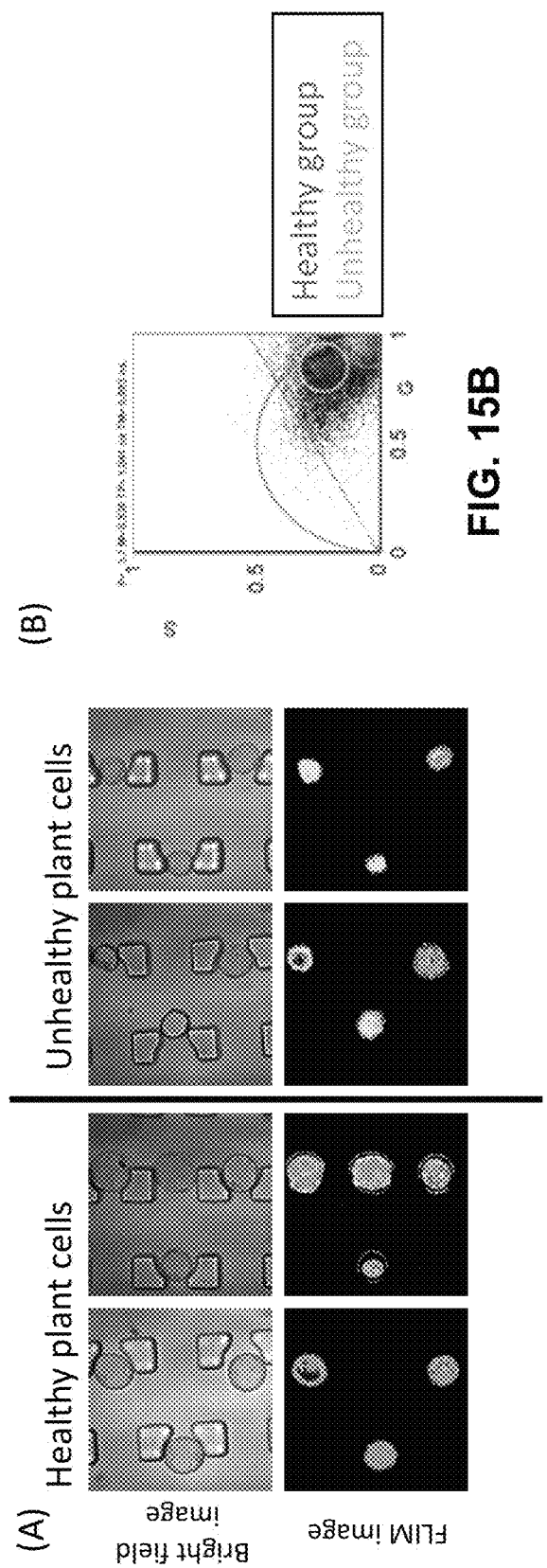
FIGS. 15A-15B show the difference between healthy and unhealthy plant cells.
Figures 16A, 16B:
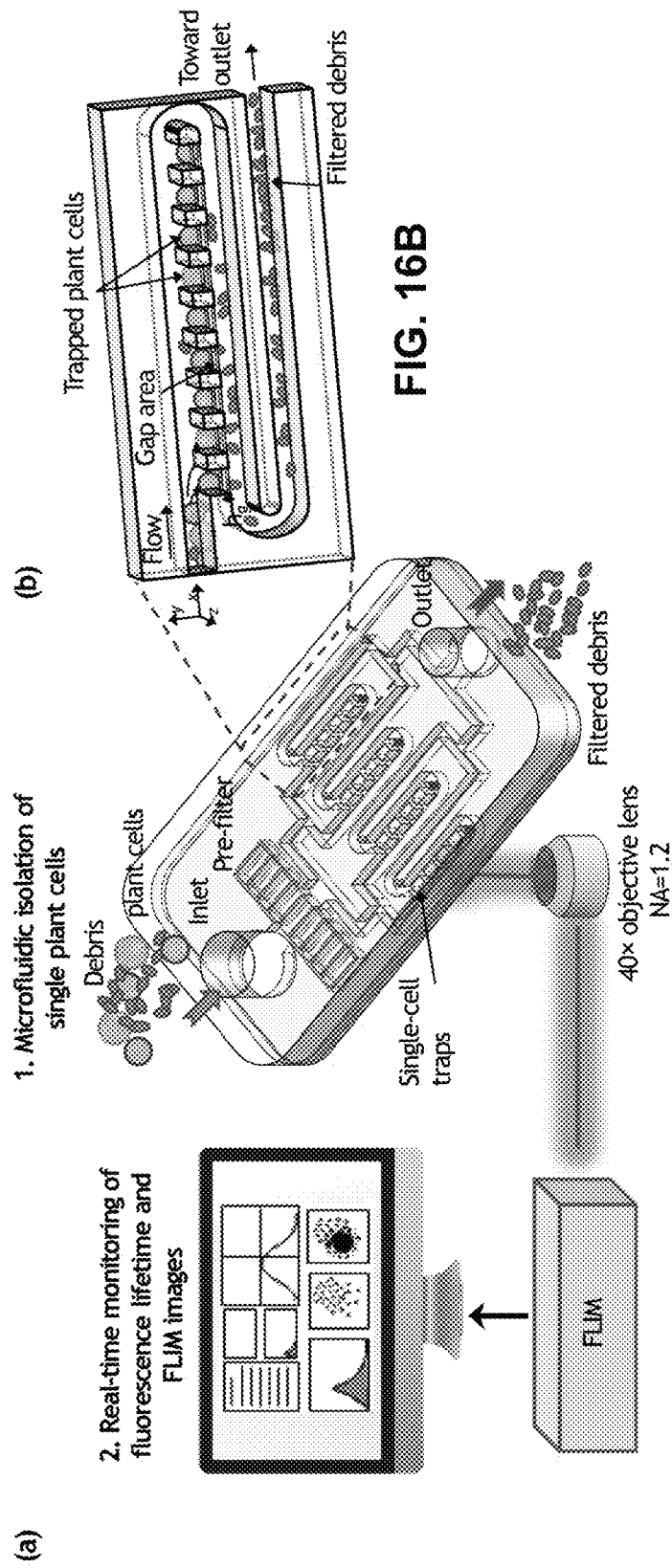
FIGS. 16A-16B show drawings of a microfluidic platform for single-plant-cell isolation and metabolic study using FLIM.
Figure 17A:
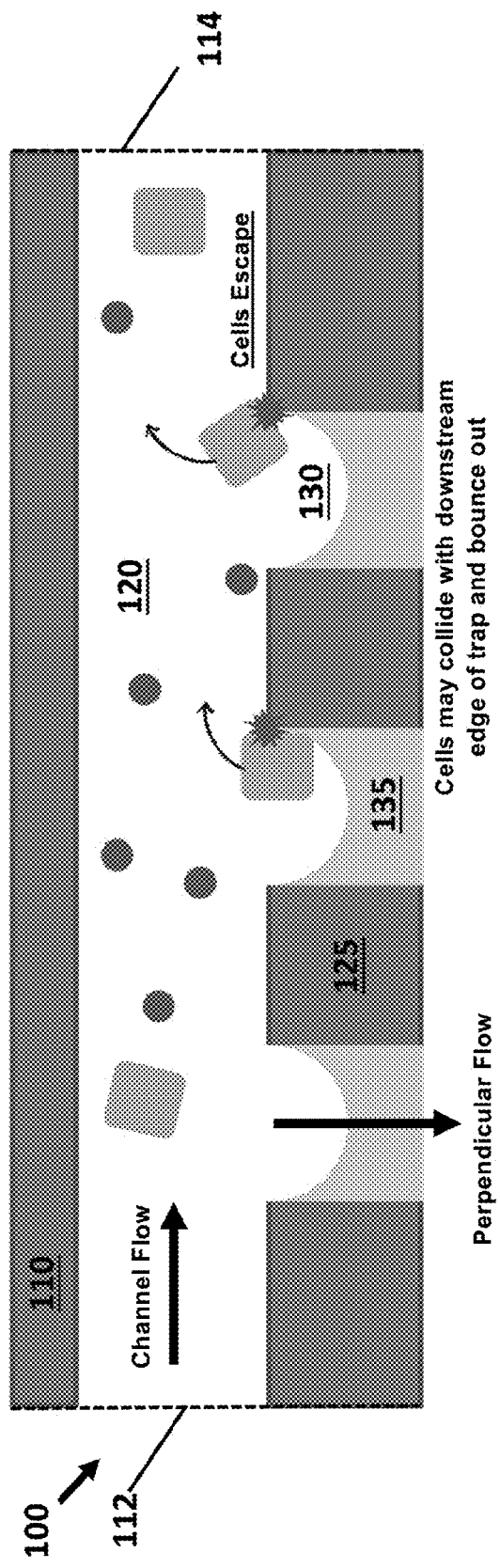
FIG. 17A shows a schematic drawing of a top view of a microfluidic device which has traps with a gap pattern which is symmetric along the channel, such that flow through the gap is substantially uniform between the upstream portion of the trap and the downstream portion of the trap. This figure illustrates that when such a device is used to trap large cells or cells with low deformability, trapping may be difficult. The cells may not completely seat within the trap as they are carried past the trap by the channel flow and then collide with the downstream edge of the trap. Where smaller, more deformable cells may deform against the edge and still be trapped, larger, less deformable cells may bounce out of the trap because of the collision.
Figure 17B:
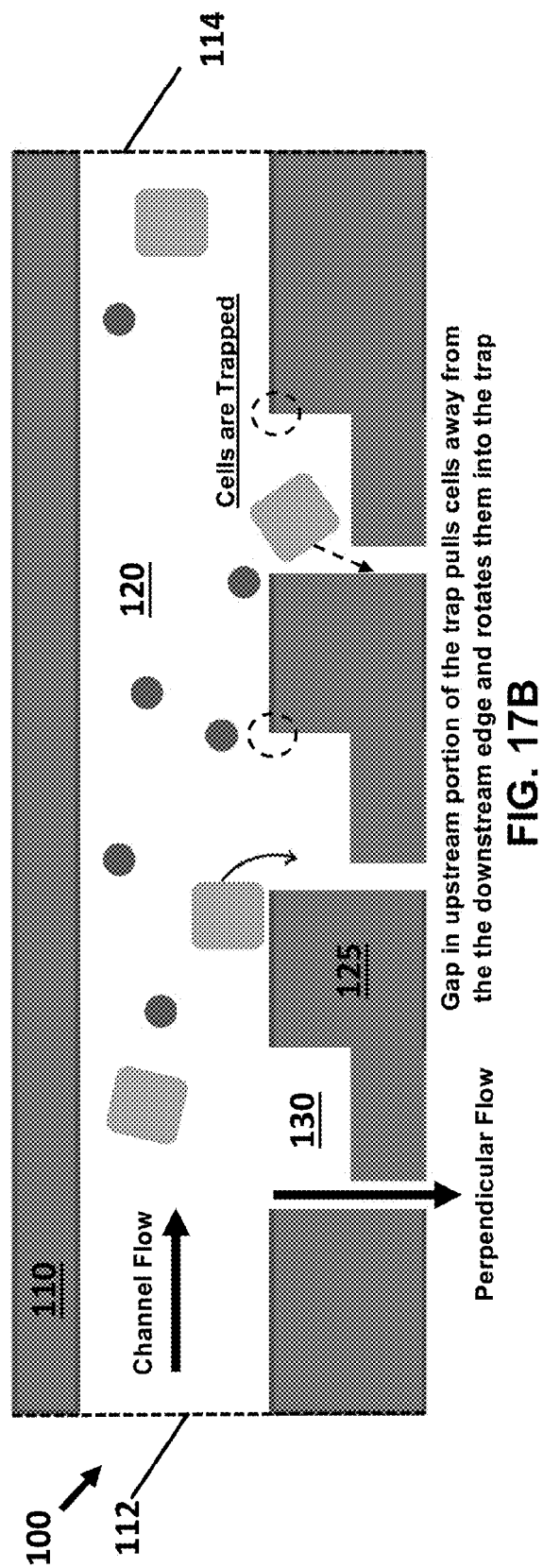
FIG. 17B shows a schematic drawing of a top view of a microfluidic device which has traps with a gap pattern which is asymmetric along the channel, such that flow through the gap is substantially different between the upstream portion of the trap and the downstream portion of the trap. More specifically, in this example the flow through the gap is focused at the upstream edge of the trap. This figure illustrates that such a device may be successfully used to trap large cells or cells with low deformability. The gap positioned in the upstream portion of the trap may cause an asymmetric flow through the trap which pulls cells away from the downstream edge of the trap and rotates them into the trap so that they are totally seated within the trap by the time they contact the downstream edge of the trap. The dotted circles illustrate that the downstream trap edges may be entirely avoided by the trapped cells.

Microfluidic Isolation and Discrimination of Healthy and Unhealthy Single Plant Cells:

The phasor-FLIM imaging is used distinguish the healthy and unhealthy plant cells (FIGS. 15A-15B). FIG. 15A shows the healthy and unhealthy late uninucleate microspores were trapped in the single-cell trapping array and imaged at 740 nm two-photon excitation. The intrinsic fluorescence emission in the range of 420 nm-500 nm was collected. And the fluorescence lifetime imaging was color-coded with the fluorescent lifetime in the corresponding phasor plots (FIG. 15B). There is a significant difference between the healthy plant cells and the unhealthy plant cells. The healthy group has a shorter lifetime which is easy to distinguish from the group of unhealthy plant cells.

Morphological Differences Between Tetrad Microspores and Late Uninucleate Microspores:

1) Chances in vacuolation: Single large vacuole in late uninucleate vs no to multiple small vacuoles in tetrad microspores. 2) Changes in nucleus orientation within cell: centralized nucleus in tetrad microspore vs migrated to perimeter, (typically distal to pore, in late uninucleate). 3) Cell wall structure: primexine or thin exine/intine in tetrad microspore vs robust exine with well-defined patterning and sporopollenin deposition in late uninucleate microspores.

Changes Associated with Healthy and Dying Cells:

1) Use FDA or propidium iodide staining of living and dead cells. 2) Changes in fluorescence with death. 3) Plasmolysis in dead/dying cells (appear desiccated and smaller). 4) Halting of cytoplasmic streaming in dead cells.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of obtaining purified viable uninucleate microspores by screening plant cells using fluorescence lifetime imaging microscopy (FLIM), the method comprising:

sorting a population of plant cells by size exclusion, said population of plant cells comprising microspores in any developmental stage, tetrads or pollen grain cells to obtain a first population of purified uninucleate microspores;

imaging the first population of purified uninucleate microspores using FLIM;

selecting a second population of purified viable uninucleate microspores from the first population of purified uninucleate microspores based on the FLIM imaging; and obtaining the second population of purified viable uninucleate microspores.

2. The method of claim 1, wherein the population of plant cells are sorted using traps, and wherein the traps each comprise a gap, resulting in a gap area or height gap (hg).

3. The method of claim 2, wherein the gap allows fluid or a plurality of smaller plant cells to flow through the gap even when the trap holds a selected plant cell.

4. The method of claim 1, wherein the FLIM imaging is non-destructive, label free, or non-invasive, and wherein the imaged population of purified uninucleate microspores are viable for further analysis or culturing.

5. The method of claim 1, wherein the method additionally comprises selecting a subset of the population of plant cells based on the analysis, and culturing the selected subset of the population of plant cells.

6. The method of claim 1, wherein the FLIM analysis is used to identify if the plant cell is healthy.

7. The method of claim 1, wherein the method additionally comprises selecting a subset of microspores of the population of plant cells based on the analysis, and aspirating mRNA from the selected subset of microspores for further analysis.

8. The method of claim 2, wherein each trap has a gap pattern which is asymmetric along a channel of the trap.

9. The method of claim 1 further comprising immobilizing a population of plant cells in a monolayer on a substrate in a microfluidic device.

10. The method of claim 1, wherein using FLIM imaging comprises using changes in vacuolization, changes in nucleus orientation, and differences in cell wall structure to image and select between tetrads and uninucleate microspores.

11. The method of claim 1 further comprising using staining, changes in fluorescence with plant cell death, plasmolysis, halting of cytoplasmic streaming, or a combination thereof to select between healthy and unhealthy plant cells.

12. The method of claim 1 further comprising imaging at a 740 nm two-photon excitation wavelength to determine plant cell health, wherein a detected emission of 420-500 nm is indicative of a healthy plant cell.

13. A method of screening plant cells using fluorescence lifetime imaging microscopy (FLIM), the method comprising:

immobilizing a population of plant cells in a monolayer on a substrate in a microfluidic device having a plurality of traps, wherein the plurality of traps each comprise a channel and a plurality of gaps, wherein one or more gaps of the plurality of gaps comprise a single notched edge, wherein the population of plant cells are sorted by size exclusion, wherein a size of the single notched edge in a gap determines a size of a plant cell able to be trapped by the gap;

imaging the population of plant cells using FLIM; and analyzing the FLIM data of a single cell or tetrad within the population of plant cells.

14. The method of claim 13 further comprising using staining, changes in fluorescence with plant cell death, plasmolysis, halting of cytoplasmic streaming, or a combination thereof to select between healthy and unhealthy plant cells.

15. The method of claim 13 further comprising imaging at a 740 nm two-photon excitation wavelength to determine plant cell health, wherein a detected emission of 420-500 nm is indicative of healthy plant cells.

* * * * *